United States Patent [19]
Ohashi et al.

[11] Patent Number: 5,648,455
[45] Date of Patent: Jul. 15, 1997

[54] ANTIBIOTIC WAP-8294A, METHOD FOR PREPARING THE SAME AND ANTIBACTERIAL COMPOSITION

[75] Inventors: Yoshitami Ohashi; Haruhisa Hirata; Seigo Nakaya; Azusa Katou; Yuji Aiba; Naomi Kokubo; Nobuyuki Suzuki; Makoto Maeda, all of Tokyo, Japan

[73] Assignee: Wakamoto Pharmaceutical Co., Ltd., Tokyo, Japan

[21] Appl. No.: 387,322

[22] Filed: Feb. 13, 1995

[30] Foreign Application Priority Data

| Feb. 18, 1994 | [JP] | Japan | 6-043314 |
| Apr. 19, 1994 | [JP] | Japan | 6-103229 |
| Feb. 2, 1995 | [JP] | Japan | 7-016044 |

[51] Int. Cl.$^6$ ................................. A61K 38/00
[52] U.S. Cl. .................................... 530/300
[58] Field of Search ............................. 530/300

[56] References Cited

U.S. PATENT DOCUMENTS

| 4,754,018 | 6/1988 | Tymiak et al. | 530/317 |
| 4,876,251 | 10/1989 | Morimoto et al. | 514/193 |
| 4,891,427 | 1/1990 | Morimoto et al. | 540/216 |

*Primary Examiner*—Edward J. Cain
*Attorney, Agent, or Firm*—Oblon, Spivak, McClelland, Maier & Neustadt, P.C.

[57] ABSTRACT

Antibiotics WAP-8294A, $A_1$, $A_2$, $A_4$, AX, AX-8, AX-9 and AX-13 or pharmeceutically acceptable salts thereof produced by a strain belonging to the genus *Lysobacter*; a method for producing the foregoing antibiotic WAP-8294A comprising the steps of cultivating, in the culture medium, a microorganism belonging to the genus *Lysobacter* and having an ability of producing the antibiotic WAP-8294A to produce the antibiotic and accumulate it in the culture medium; then recovering the antibiotic; as well as an antibacterial composition comprising the antibiotic or pharmaceutically acceptable salts thereof are herein disclosed. The novel antibiotic WAP-8294A has an excellent therapeutic effect on infectious diseases developed by infection with Gram-positive bacteria, in particular, MRSA and, therefore, the antibiotic is effective for treating diseases including MRSA infectious diseases developed through infection with Gram-positive bacteria as infectious bacteria.

12 Claims, 9 Drawing Sheets

ANTIBIOTIC WAP-8294A, METHOD FOR PREPARING THE SAME AND ANTIBACTERIAL COMPOSITION

BACKGROUND OF THE INVENTION

The present invention relates to a novel antibiotic WAP-8294A useful as agents for treating diseases developed by infection with pathogenic microorganisms, a method for producing the same and the use thereof.

Since the history of chemotherapeutic agents for bacterial infectious diseases started with the synthesis of quinine and salvarsan and the discovery of penicillin, mankind has been graced with these chemotherapeutic agents. Recently, however, there emerges the existence of these chemotherapeutic agents resistant bacteria, as is represented by the infectious disease with MRSA (methicillin-resistant Staphylococcus aureus), on which chemotherapeutic agents other than Vancomycin and Habekacin have no effect, this leads to confusion in the field of medical treatment and constitutes a severe social problem.

Vancomycin as an antibiotic was developed by Eli Lilly & Co. in the United States and has been used for treating MRSA infectious diseases, but such treatment is often accompanied by nephrotoxicity, hepatotoxicity and even cranial nerve VIII (nervus octavus) disorders(ototoxicity) and requires a long pasteurization-accomplishing time and there has been a suspicion that bacteria resistant to this antibiotic again appear.

On the other hand, Habekacin is a chemically derived (from) antibiotic which has a skeleton of Kanamycin as one of aminoglycoside antibiotics, and has an excellent antibiotic action and an effect on various kinds of resistant bacteria and accordingly, used as one of a limited number of chemotherapeutic agents for treating MRSA infectious diseases, but the use thereof may sometimes be accompanied by severe nethrotoxicity and cranial nerve VIII disorders (ototoxicity) as the side-effects peculiar to the aminoglycoside antibiotics and therefore, this is not necessarily a safe antibiotic from the standpoint of medical treatments.

Under such circumstances, there has everlastingly been desired for the discovery and development of a novel chemotherapeutic agent having low toxicity, showing its antibiotic action within a short time period and having almost no side effect and many investigations have been made to solve such a problem.

SUMMARY OF THE INVENTION

An object of the present invention is to provide a novel antibiotic having an antibacterial activity which permits the satisfaction of the foregoing requirements. Another object of the present invention is to provide a method for preparing the antibiotics. A still another object of the present invention is to provide a clinically useful chemotherapeutic agent having a lower toxicity or an excellent selective toxicity.

The inventors of this invention have conducted various studies to discover a novel and useful antibiotic, as a result, have succeeded in the isolation of a strain belonging to the genus Lysobacter from the soil as a novel microorganism, found out that the strain produces an antibiotic undescribed in the literature and thus have completed the present invention.

The present invention thus relates to an antibiotic WAP-8294A or pharmaceutically acceptable salts thereof having physicochemical properties as will be detailed later. The present invention also relates to a method for producing the foregoing antibiotic WAP-8294A which comprises the steps of cultivating, in a culture medium, a microorganism belonging to the genus Lysobactor and having an ability of producing the antibiotic WAP-8294A to produce the antibiotic and accumulate it in the culture medium; then recovering the antibiotic; a microorganism belonging to the genus Lysobactor and having an ability of producing the antibiotic WAP-8294A; and an antibacterial composition comprising at least one member selected from the group consisting of the antibiotic WAP-8294A and pharmaceutically acceptable salts thereof.

DESCRIPTION OF THE PREFERRED EMBODIMENTS

The present invention relates to a novel antibiotic WAP-8294A found in the culture medium of a novel strain belonging to the genus Lysobacter. The antibiotic WAP-8294A is further fractionated into at least seven components AX, $A_1$, $A_2$, $A_3$, $A_4$, $A_5$ and $A_6$ and the component AX is further fractionated into at least 13 components AX-1, AX-2, AX-3, AX-4, AX-5, AX-6, AX-7, AX-8, AX-9, AX-10, AX-11, AX-12 and AX-13. The term "antibiotic WAP-8294A" herein used means the foregoing components AX, $A_1$, $A_2$, $A_3$, $A_4$, $A_5$, $A_6$, AX-1, AX-2, AX-3, AX-4, AX-5, AX-6, AX-7, AX-8, AX-9, AX-10, AX-11, AX-12, AX-13 or a mixture thereof.

The present invention also encompasses, in addition to the antibiotic WAP-8294A in the free form, pharmaceutically acceptable salts thereof such as hydrochlorides, sulfates and methanesulfonates.

These substances show strong antibacterial activity against Gram-positive bacteria, in particular, methicillin-resistant Staphylococcus aureus (MRSA).

Figure 1:
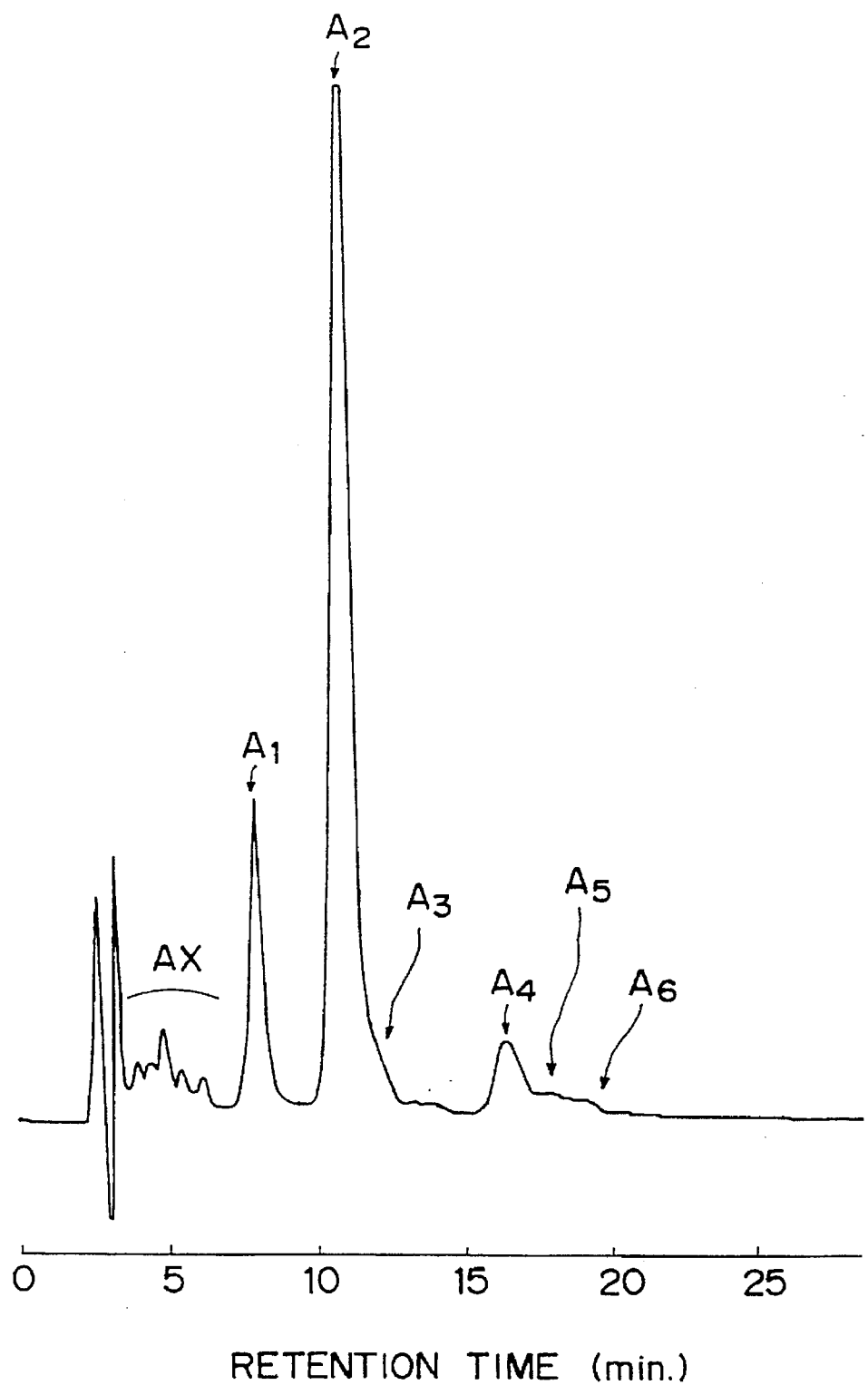
FIG. 1 is a chromatogram observed when the antibiotic WAP-8294A are separated into a series of fractions through high performance liquid chromatography.

The antibiotic WAP-8294A is separated into fractions having retention time of 4.0 to 6.1 minutes, 8.0 minutes, 11.1 minutes, 12.5 minutes, 16.5 minutes, 17.9 minutes and 18.8 minutes observed under elution conditions for the $C_{18}$ reverse phase silica gel-high perfromance liquid chromatography [column: YMC A-312 (6×150 mm); mobile phase: 0.05% trifluoroacetic acid-containing acetonitrile: water (45 : 55); detection wavelength: UV 214 nm; flow rate: 1 ml/min], i.e., components AX, $A_1$, $A_2$, $A_3$, $A_4$, $A_5$ and $A_6$ (FIG. 1).

Figure 6:
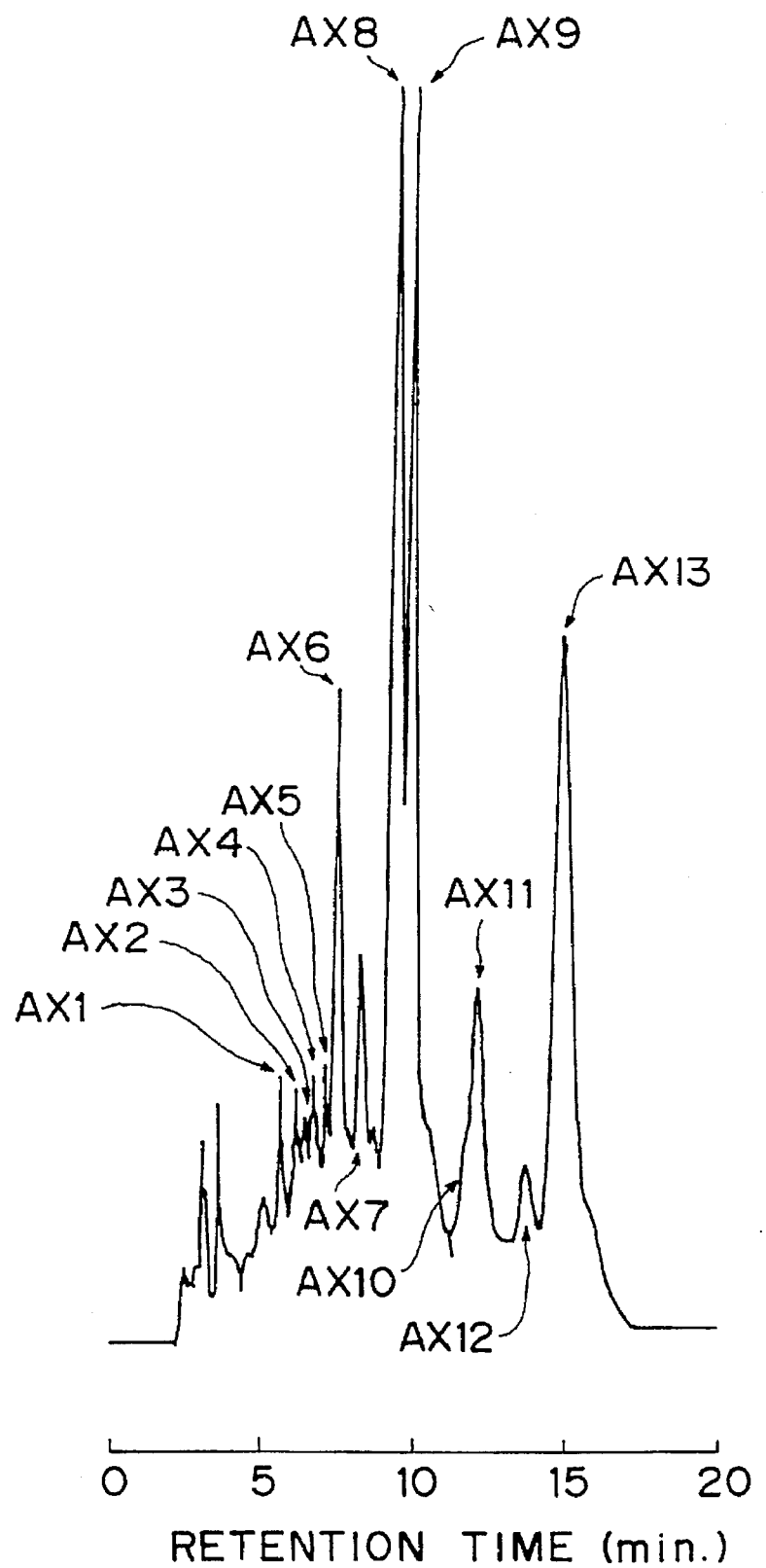
FIG. 6 is a chromatogram observed when the antibiotic WAP-8294AX is separated through high performance liquid chromatography.

The fraction AX is, as shown in FIG. 6, further separated into fractions having retention time of 5.3 minutes, 5.9 minutes, 6.2 minutes, 6.5 minutes, 6.9 minutes, 7.3 minutes, 8.1 minutes, 9.3 minutes, 9.8 minutes, 11.3 minutes, 12.1 minutes, 13.7 minutes and 15.0 minutes observed under elution conditions for the $C_{18}$ reverse phase silica gel-high perfromance liquid chromatography [column: YMC A-312 (6×150 mm); mobile phase: 0.05% trifluoroacetic acid-containing acetonitrile: water (37 : 63); detection wavelength: UV 214 nm; flow rate: 1 ml/min], i.e., components AX-1, AX-2, AX-3, AX-4, AX-5, AX-6, AX-7, AX-8, AX-9, AX-10, AX-11, AX-12 and AX-13.

Figure 2:
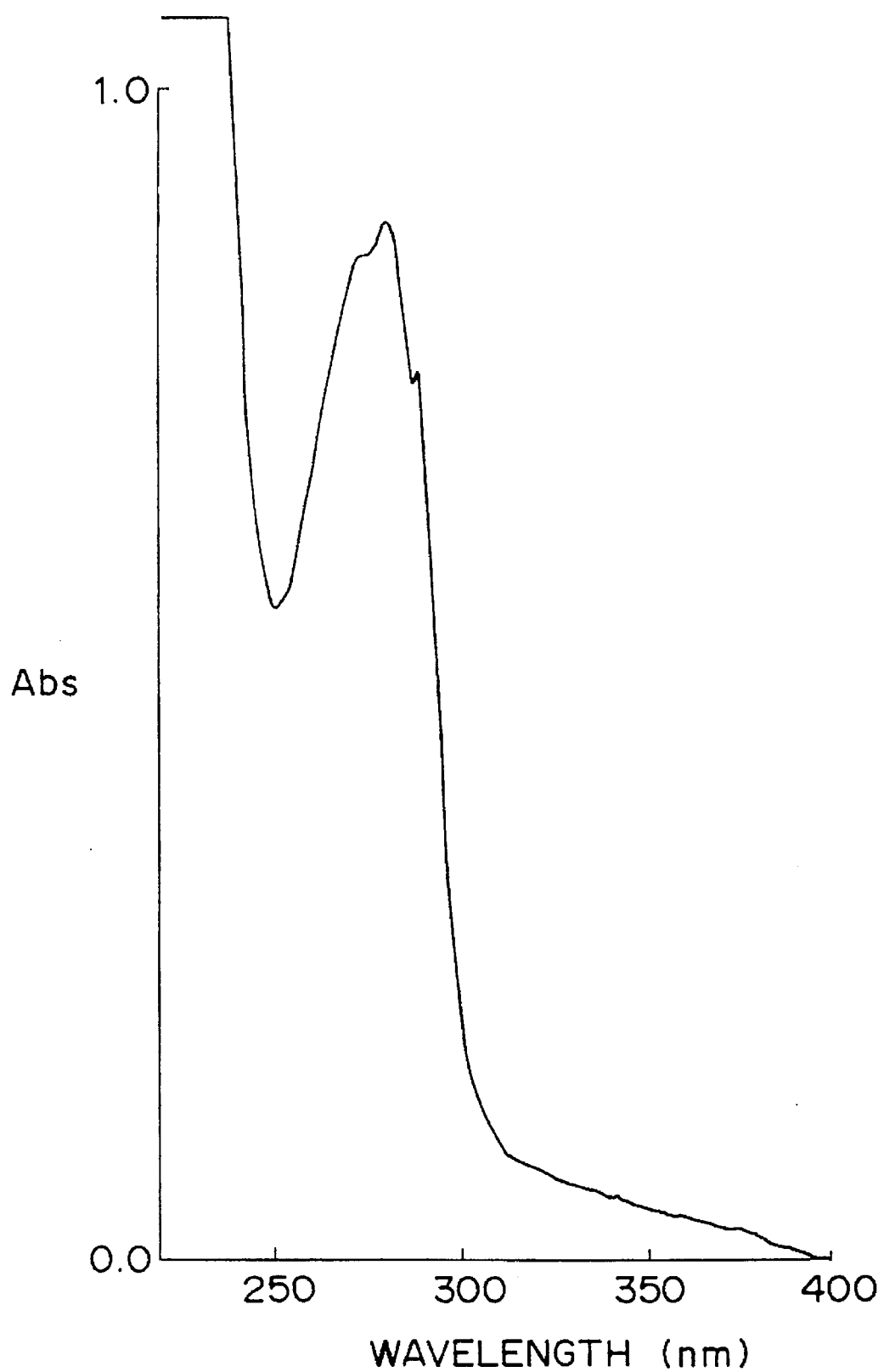
FIG. 2 is a diagram showing UV absorption spectrum(in water) of the antibiotic WAP-8294$A_2$ (hydrochloride).

The antibiotics WAP-8294A, $A_1$, $A_2$ and $A_4$ have ultraviolet absorption spectra (in water) at $\lambda_{max}$ of 275 nm, 280 nm and 287 nm. The ultraviolet absorption spectrum chart of the antibiotic WAP-8294$A_2$ is shown in FIG. 2. It also becomes clear that the antibiotics WAP-8294A, $A_1$, $A_2$ and $A_4$ comprise tryptophan as a chromophore in the molecules as is confirmed by the analysis of acid-hydrolyzates thereof as will be detailed later.

Figure 3:
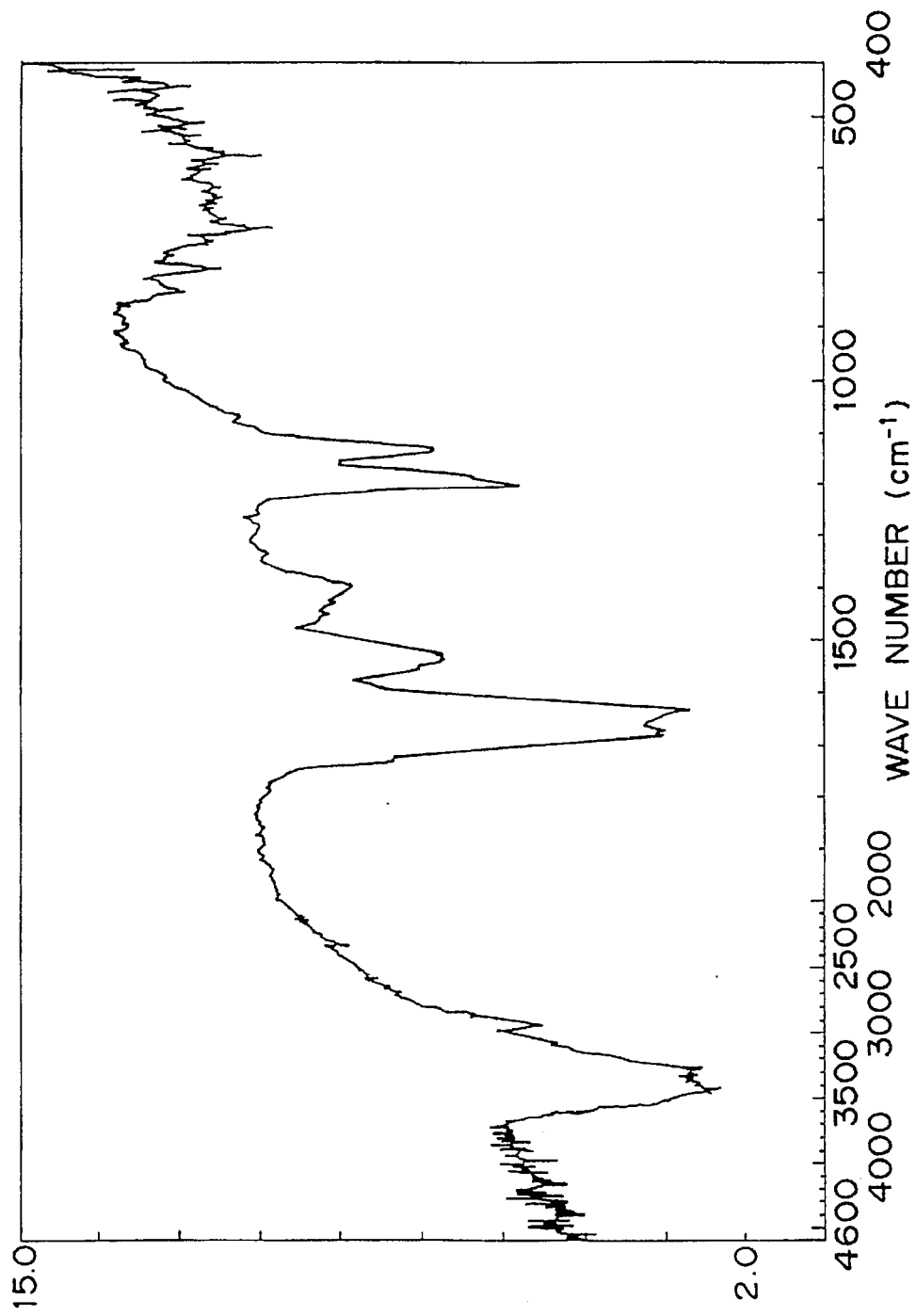
FIG. 3 is a diagram showing IR absorption spectrum(FT-IR, KBr) of the antibiotic WAP-8294$A_2$ (hydrochloride).

The infrared absorption spectroscopic analysis of the antibiotics WAP-8294A, $A_1$, $A_2$ and $A_4$ shows absorbance at 3300 $cm^{-1}$ ascribed to OH and NH groups; 1720 to 1715 $cm^{-1}$ ascribed to carboxyl or estercarbonyl groups; 1636 and 1541 $cm^{-1}$ ascribed to amido bonds; and 1207 and 1137 $cm^{-1}$ ascribed to the C-O stretching vibrations, but they do not have any other characteristic absorbance. The IR absorption spectrum of the antibiotic WAP-8294$A_2$ is shown in FIG. 3.

Figure 4:
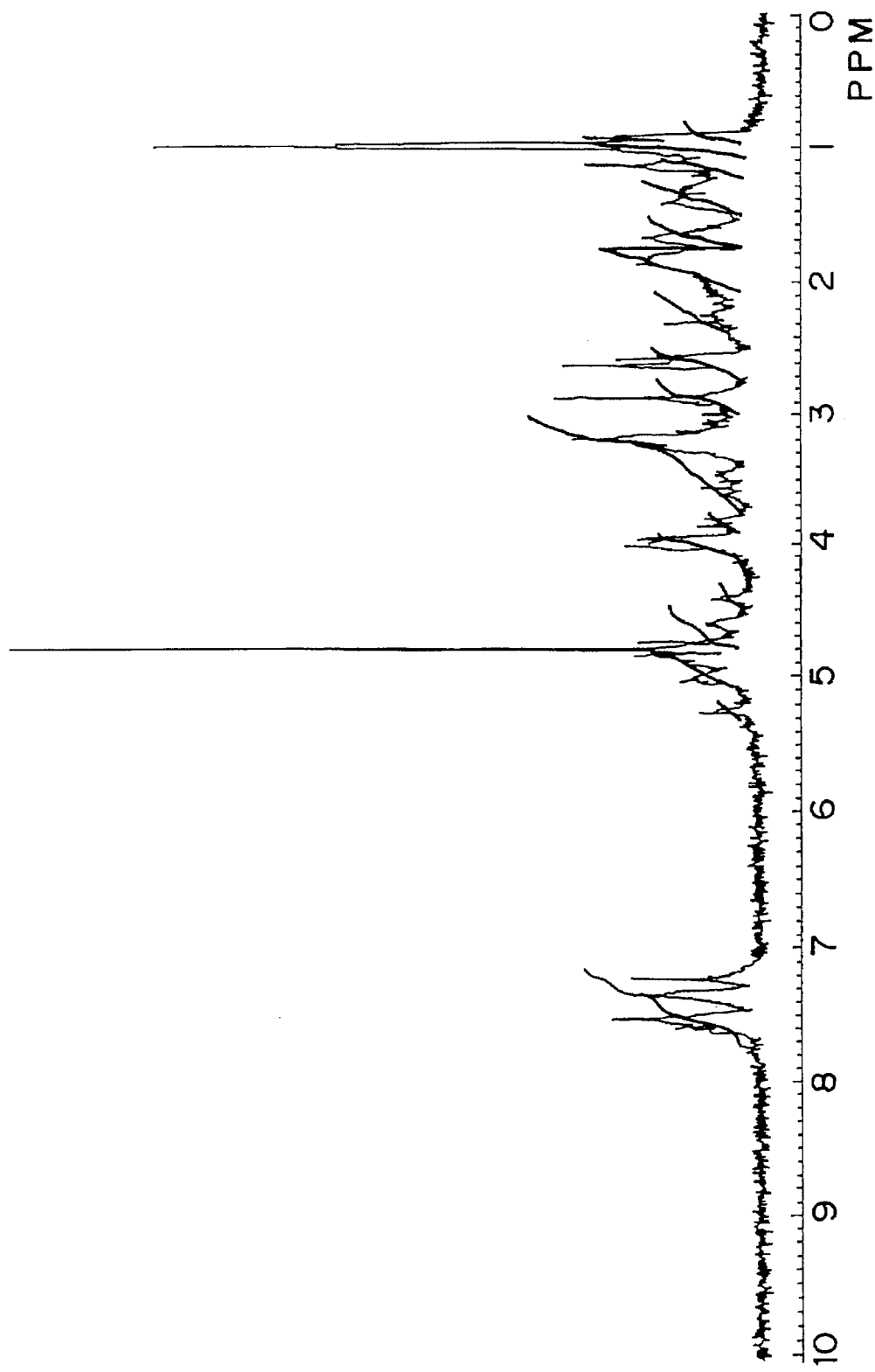
FIG. 4 is a diagram showing $^1$H-NMR spectrum (270 MHz, $D_2O$) of the antibiotic WAP-8294$A_2$ (hydrochloride).

In the $^1$H-NMR spectroscopic measurement of the antibiotics WAP-8294A, $A_1$, $A_2$ and $A_4$, there are observed a number of complicated proton signals originated from methyl, methylene, methine, and heterocycles or aromatic rings. The $^1$H-NMR spectrum chart of the antibiotic WAP-8294$A_2$ is shown in FIG. 4.

The FAB-mass-spectrometric measurement of the WAP-8294$A_1$, $A_2$ and $A_4$ indicates that the $(M+H)^+$ ion of the component $A_1$ has an m/z of 1548.9, the $(M+H)^+$ ion of the component $A_2$ has an m/z of 1562.9 and the $(M+H)^+$ ion of the component $A_4$ has an m/z of 1576.9, and the results of the sodium-melting test of the components $A_1$, $A_2$ and $A_4$ make it clear that these components each is a compound comprising carbon, hydrogen, oxygen and nitrogen elements. The following molecular formulae listed in Table 1 would be deduced from these facts while taking into consideration the structure estimation and molar ratios of all of the amino acids and fatty acids constituting these components as will be detailed later as well as the results of high resolution FAB-mass-spectrometric measurements.

Figure 5:
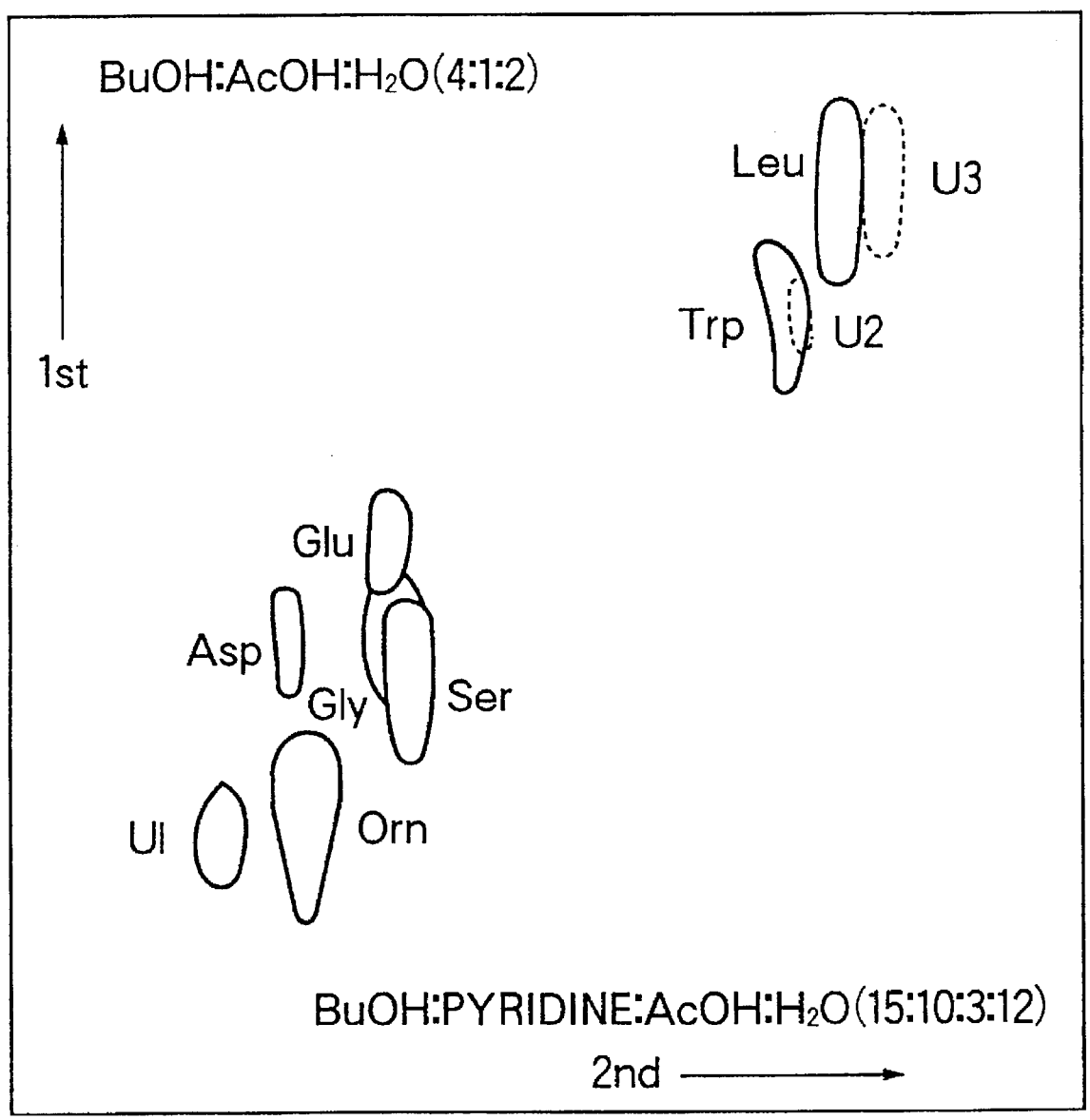
FIG. 5 shows a two-dimensional TLC chromatogram of acid-complete hydrolyzate of the antibiotic WAP-8294A.

The antibiotics WAP-8294A, $A_1$, $A_2$ and $A_4$ are positive in ninhydrin, Ehrlich, Rydon-Smith, iodine vapor, potassium permanganate aqueous solution and sulfuric acid reactions; exhibit quenching spots through irradiation with light rays of 254 nm emitted from a UV lamp; and are negative in Molisch, silver nitrate, ferric chloride and Dragendorff's reactions. Moreover, to examine the amino acid compositions of the antibiotics WAP-8294A, $A_1$, $A_2$ and $A_4$, each of them was completely hydrolyzed with an acid and then subjected to two-dimensional TLC and amino acid analysis and the results thus obtained indicate that either of them comprises aspartic acid (Asp), glutamic acid (Glu), glycine (Gly), leucine (Leu), serine (Ser), tryptophan (Trp) and ornithine (Orn) as well as 3 unknown amino acids. The result of the two-dimensional TLC analysis of the antibiotic WAP-8294A is shown in FIG. 5.

Thus, unknown amino acid-1, unknown amino acid-2 and unknown amino acid-3 were isolated by again hydrolyzing the WAP-8294A with an acid in order to identify these unknown amino acids. The unknown amino acid-1, -2 and -3 were found to be β-hydroxyaspartic acid, N-methylvaline and N-methylphenylalanine respectively on the basis of the results of various instrumental analyses.

On the other hand, 3-hydroxyoctanoic acid, 3-hydroxy-7-methyloctanoic acid or 3-hydroxy-8-methylnonanoic acid was isolated from the ether extract of each solution obtained by acid-hydrolysis of the individual component WAP-8294$A_1$, $A_2$ or $A_4$.

Furthermore, the antibiotic WAP-8294AX was separated into at least 13 fractions, i.e., AX-1: retention time 5.3 min; AX-2: retention time 5.9 min; AX-3: retention time 6.2 min; AX-4: retention time 6.5 min; AX-5: retention time 6.9 min; AX-6: retention time 7.3 min; AX-7: retention time 8.1 min; AX-8: retention time 9.3 min; AX-9: retention time 9.8 min; AX-10: retention time 11.3 min; AX-11: retention time 12.1 min; AX-12: retention time 13.7 min; and AX-13: retention time 15.0 min as is clear from the chromatogram of $C_{18}$, reverse phase silica gel-high performance liquid chromatography shown in FIG. 6.

Figure 7:
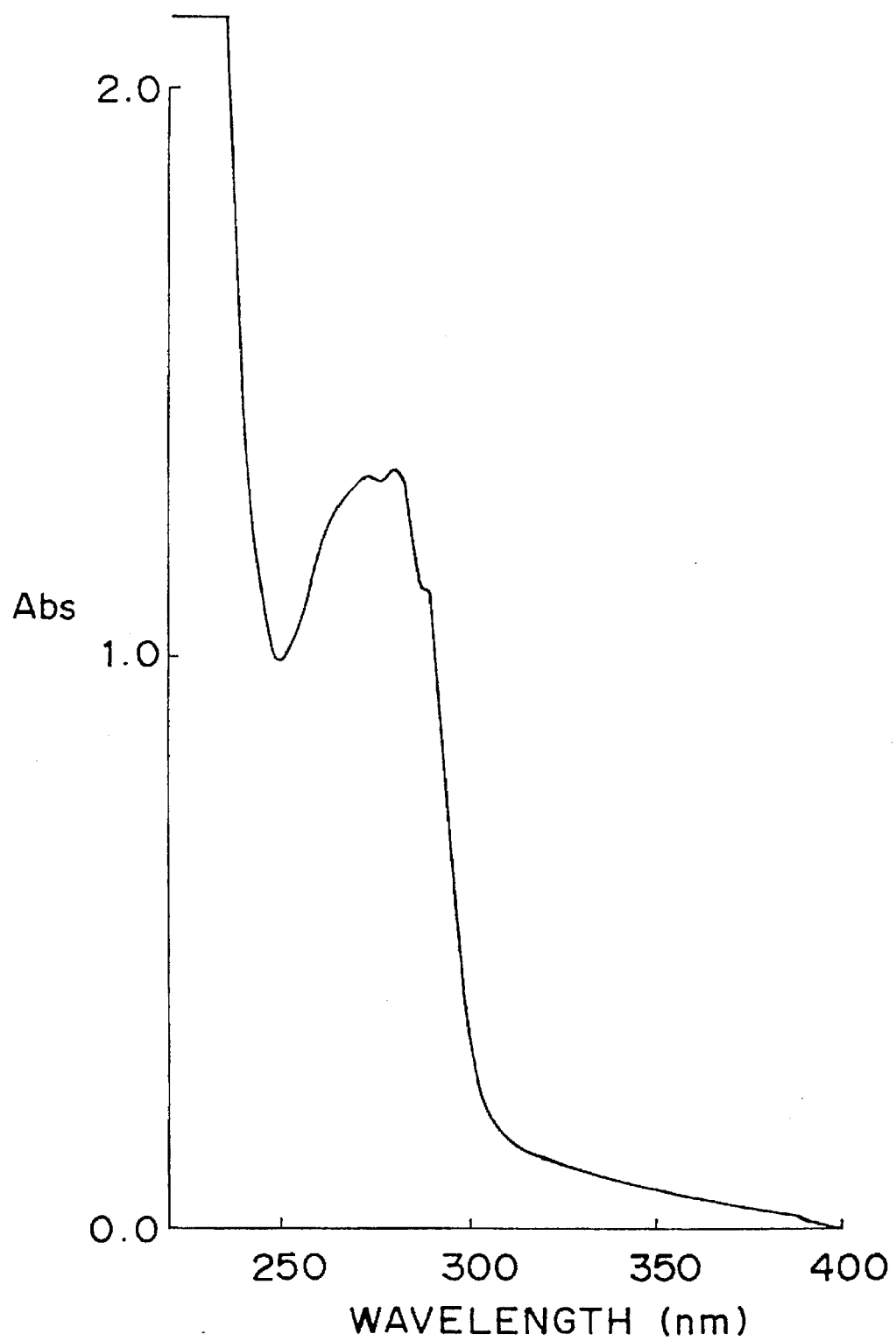
FIG. 7 is a diagram showing UV absorption spectrum(in water) of the antibiotic WAP-8294AX-8 (hydrochloride).

The antibiotics WAP-8294AX, AX-8, AX-9 and AX-13 have ultraviolet absorption spectra (in water) at $\lambda_{max}$ of 273 nm, 280 nm and 289 nm. It also becomes clear that the WAP-8294AX, AX-8, AX-9 and AX-13 comprise one mole of tryptophan as a chromophore in the molecules as is confirmed by the analysis of acid-hydrolyzates thereof as will be detailed later. The ultraviolet absorption spectrum chart of the antibiotic WAP-8294AX-8 is shown in FIG. 7.

Figure 8:
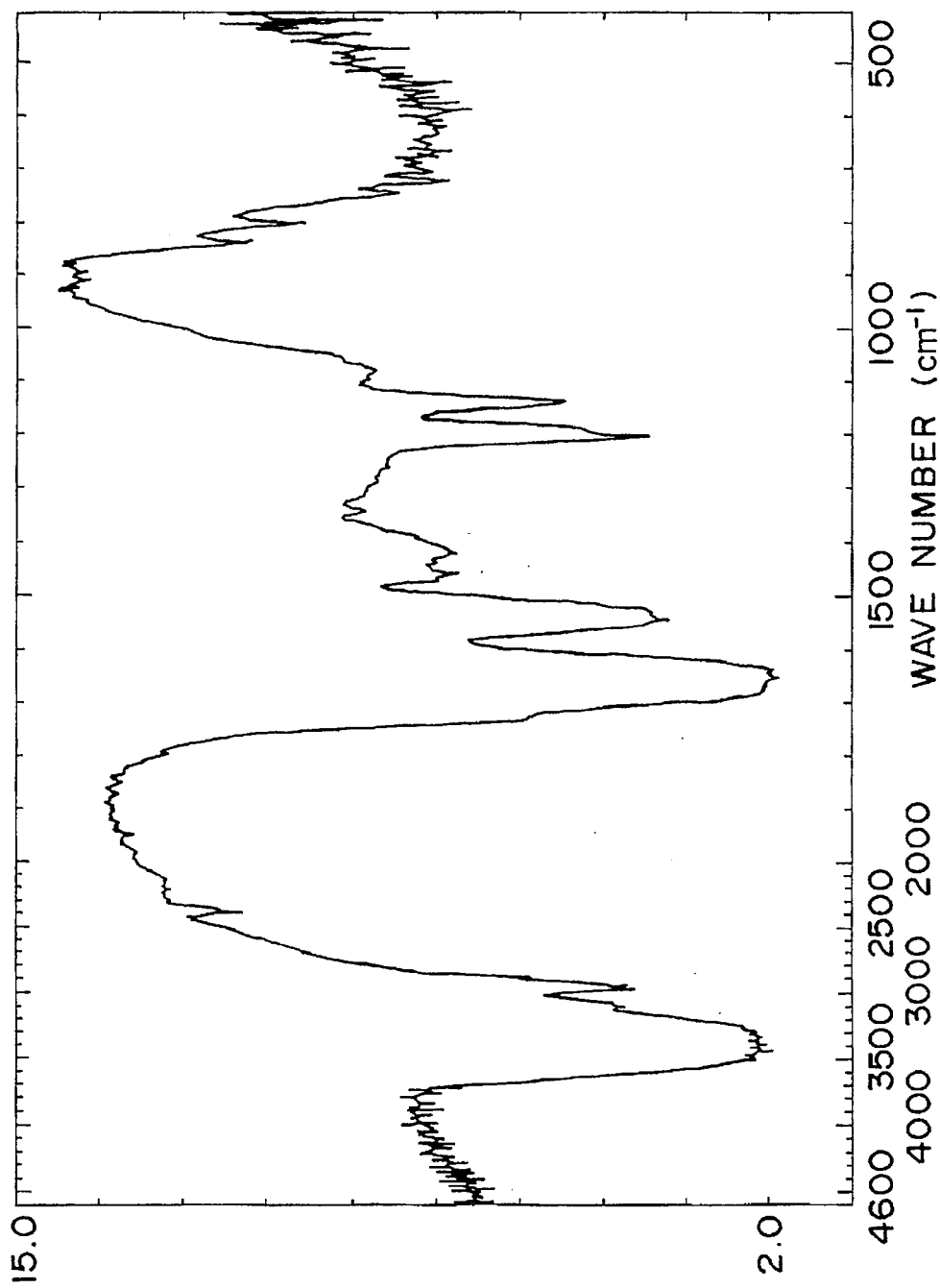
FIG. 8 is a diagram showing IR absorption spectrum(FT-IR, KBr) of the antibiotic WAP-8294AX-8 (hydrochloride).

The infrared absorption spectroscopic analysis of the antibiotics WAP-8294AX, AX-8, AX-9 and AX-13 shows absorbance at 3300 $cm^{-1}$ ascribed to OH and NH groups; 1720 to 1715 $cm^{-1}$ ascribed to carboxyl or estercarbonyl groups; 1636 and 1541 $cm^{-1}$ ascribed to amido bonds; and 1207 and 1137 $cm^{-1}$ ascribed to the C-O stretching vibrations, but they do not have any other characteristic absorbance. The IR absorption spectrum chart of the antibiotic WAP-8294AX-8 is shown in FIG. 8.

TABLE 1

| | $A_1$ | $A_2$ | $A_4$ |
|---|---|---|---|
| FAB-Mass $(M + H)^+$ | 1548.9 | 1562.9 | 1576.9 |
| FAB-Mass $(M - H)^-$ | 1546.7 | 1561.2 | 1575.4 |
| Δ Mass Unit | | 14 mass units | 14 mass units |
| | | $A_1$------>$A_2$ | $A_2$------>$A_4$ |
| Molecular Weight | 1547.9 | 1561.9 | 1575.9 |
| HR-FAB-Mass | 1548.8088 | 1562.8224 | 1576.8363 |
| Molecular Formula | $C_{72}H_{109}O_{21}N_{17}$ | $C_{73}H_{111}O_{21}N_{17}$ | $C_{74}H_{113}O_{21}N_{17}$ |

Figure 9:
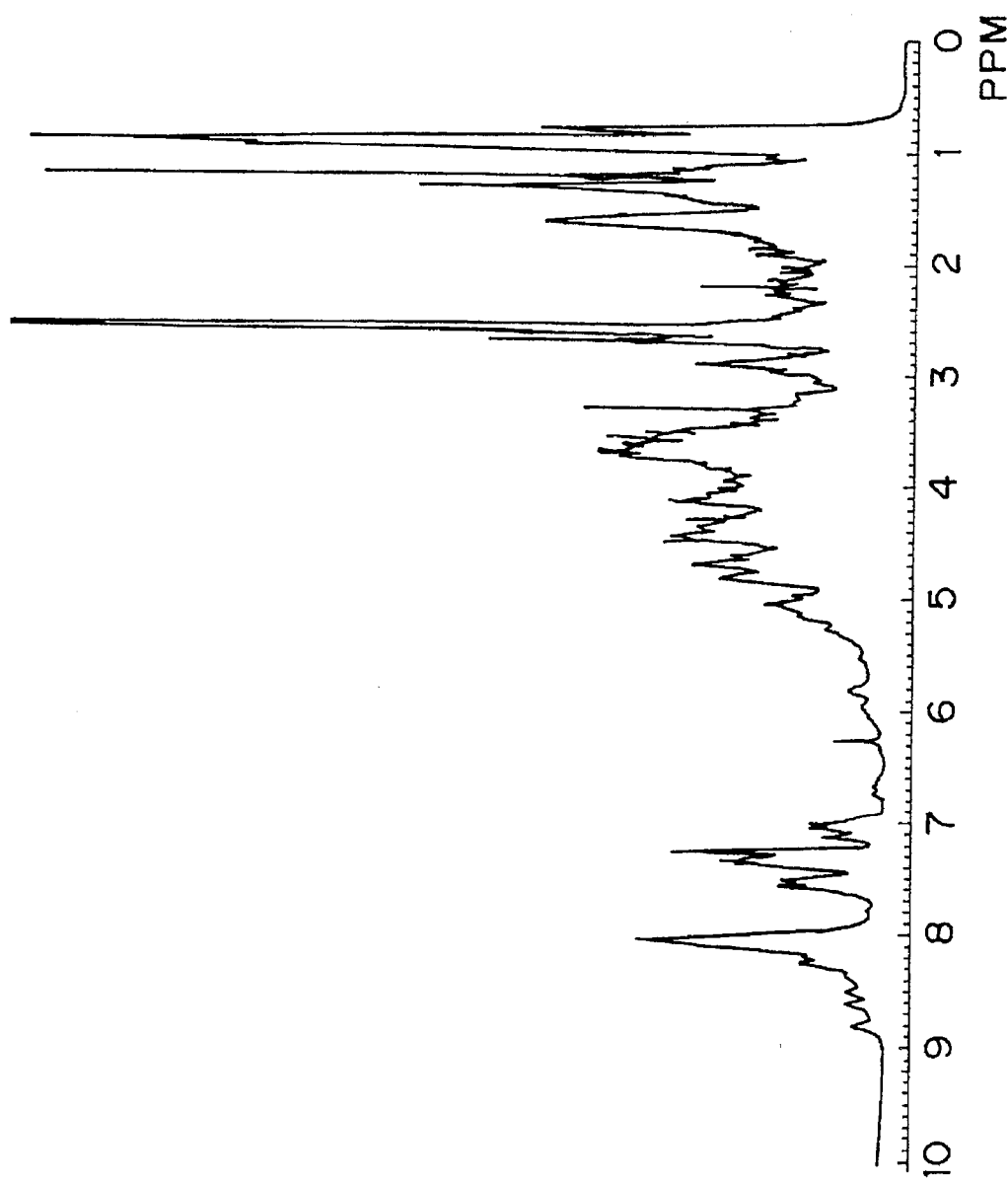
FIG. 9 is a diagram showing $^1$H-NMR spectrum(270 MHz, $D_2O$) of the antibiotic WAP-8294AX-8 (hydrochloride).

In the $^1$H-NMR spectroscopic measurement of the antibiotics WAP-8294AX, AX-8, AX-9 and AX-13, there are observed a number of complicated proton signals originated from methyl, methylene, methine, and heterocycles or aromatic rings. The $^1$H-NMR spectrum chart of the antibiotic WAP-8294AX-8 is shown in FIG. 9.

The FAB-mass-spectrometric measurement of the WAP-8294AX-8, AX-9 and AX-13 indicates that the $(M+H)^+$ ion of the component AX-8 has an m/z of 1549, the $(M+H)^+$ ion of the component AX-9 has an m/z of 1549 and the $(M+H)^+$ ion of the component AX-13 has an m/z of 1577, and the results of the sodium-melting test of the components AX-8, AX-9 and AX-13 make it clear that these components each is a compound comprising carbon, hydrogen, oxygen and nitrogen elements. The following molecular formulae listed in Table 2 would be deduced from these facts while taking into consideration the structure estimation and molar ratios of all of the amino acids and fatty acids constituting these components as well as the results of high resolution FAB-mass-spectrometric measurements, as will be detailed later.

that the WAP-8294AX comprised, as amino acids positive in the ninhydrin reaction, aspartic acid (Asp), glutamic acid (Glu), glycine (Gly), β-alanine (β-Ala), leucine (Leu), serine (Ser), tryptophan (Trp), ornithine (Orn), valine (Val), N-methylvaline (N-MeVal), β-hydroxyaspartic acid (β-OH-Asp), phenylalanine (Phe) and N-methylphenylalanine (N-MePhe).

On the other hand, it was also confirmed that the ether extract of the acid-complete hydrolyzate of the antibiotic WAP-8294AX contained 3-hydroxy-7-methyloctanoic acid.

The antibiotics WAP-8294AX-8, AX-9 and AX-13 were treated by the same procedures used for the treatment of the antibiotic WAP-8294AX and the amino acids and fatty acids constituting these components could be identified on the basis of the two-dimensional TLC analysis, amino acid analysis, and GC-Mass analysis of the ether extract of the acid-complete hydrolyzates. The results are listed in Table 3 along with the results observed for the antibiotic WAP-8294A$_2$.

TABLE 2

| Component | AX-8 | AX-9 | AX-13 |
|---|---|---|---|
| FAB-Mass $(M + H)^+$ | 1549 | 1549 | 1577 |
| FAB-Mass $(M - H)^-$ | — | 1547 | — |
| Mass Unit | −14 mass units | −14 mass units | +14 mass units |
|  | A$_2$------>AX-8 | A$_2$------>AX-9 | A$_2$------>AX-13 |
| Molecular Weight | 1548 | 1548 | 1576 |
| HR-FAB-Mass | 1548.8079 | 1548.8065 | 1576.8324 |
| Molecular Formula | $C_{72}H_{109}O_{21}N_{17}$ | $C_{72}H_{109}O_{21}N_{17}$ | $C_{74}H_{113}O_{21}N_{17}$ |

The antibiotics WAP-8294AX, AX-8, AX-9 and AX-13 are positive in ninhydrin, Ehrlich, Rydon-Smith, iodine vapor, potassium permanganate aqueous solution and sulfuric acid reactions; exhibit quenching spots through irradiation with light rays of 254 nm emitted from a UV lamp; and are negative in Molisch, silver nitrate, ferric chloride and Dragendorff's reactions.

To examine the amino acid compositions of the antibiotics WAP-8294AX, AX-8, AX-9 and AX-13, each of them was completely hydrolyzed with an acid and then subjected to two-dimensional TLC analysis [cellulose plate; solvent 1: n-butanol: acetic acid: water (4 : 1 : 2); solvent 2: n-butanol: pyridine: acetic acid : water (15 : 10 : 3 : 12); spray reagent: ninhydrin and amino acid analysis. As a result, it was found

TABLE 3

| | Amino Acids and Fatty Acids Constituting Each Fraction (Molar number is given in the parentheses) | | | |
|---|---|---|---|---|
| Component | AX-8 | AX-9 | AX-13 | A$_2$ (main Component) |
| Amino Acid | Asp(1) | Asp(1) | Asp(1) | Asp(1) |
| | Ser(2) | Ser(2) | Ser(2) | Ser(2) |
| | Glu(1) | Glu(1) | Glu(1) | Glu(1) |
| | Gly(1) | Gly(1) | β-Ala(1) | Gly(1) |
| | Leu(1) | Leu(1) | Leu(1) | Leu(1) |
| | Trp(1) | Trp(1) | Trp(1) | Trp(1) |
| | Orn(2) | Orn(2) | Orn(2) | Orn(2) |
| | β-OH-Asp(1) | β-OH-Asp(1) | β-OH-Asp(1) | β-OH-Asp(1) |
| | Val(1) | N-MeVal(1) | N-MeVal(1) | N-MeVal(1) |
| | N-MePhe(1) | Phe(1) | N-MePhe(1) | N-MePhe(1) |
| Fatty Acid | 3H-7M-OA (1) | 3H-7M-OA (1) | 3H-7M-OA (1) | 3H-7M-OA (1) |

Note: 3H-7M-OA represents 3-hydroxy-7-methyloctanoic acid.

The inventors searched for known compounds on the basis of the foregoing physicochemical properties and knowledges about the acid complete-hydrolyzates of the antibiotics WAP-8294A, A$_1$, A$_2$, A$_4$, AX, AX-8, AX-9 and AX-13, amino acids and fatty acids constituting these antibiotics and as a result, secured the positive evidence of the fact that they are novel substances undescribed in the literature.

The antibiotics WAP-8294A, $A_1$, $A_2$, $A_4$, AX, AX-8, AX-9 and AX-13 of the present invention can be prepared by a method comprising the steps of cultivating, in a culture medium, an antibiotic WAP-8294A-producing bacterium belonging to the genus *Lysobactor* and isolating and collecting the antibiotic WAP-8294A and, if necessary, additionally separating and purifying it. An example of WAP-8294A-producing bacteria belonging to the genus *Lysobacter* is a *Lysobacter* sp. WAP-8294 strain isolated by the inventors of this invention from the soil originated from Shimoda City, Shizuoka Prefecture, Japan. The taxonomic bacteriological properties of the strain are as follows:

1. Morphology:

The strain was cultured at 25° C. for 3 days on a bouillon-agar plate, observed under a microscope and found to be a rod-like cell having a diameter ranging from 0.4 to 0.6 μm and a length ranging from 3.2 to 4.2 μm. The strain is Gram-negative bacterium, free of flagellum, but shows gliding movement, does not form any spore and is free of acid fastness.

2. Growth Characteristics in a Variety of Culture Media

The strain was cultured at 25° C. in a variety of culture media and observed for 3 to 14 days.

(1) Bouillon-Agar-Plate Culture

The colony formed has a translucent pale yellow circular shape, a convex circular surface and an entire to wavy periphery. The strain does not form any diffusible pigment.

(2) Bouillon-Agar-Slant Culture

The strain grows in the form of a spreaded cloth and has a translucent pale yellow color.

(3) Bouillon Liquid Culture

The medium becomes slightly turbid, the strain forms a fairy ring and there is observed precipitates of bacterial cells on the bottom periphery of the culture container.

(4) Bouillon-Gelatin Stab Culture

The strain grows within a region extending from the surface to the middle of the medium while liquefying the gelatin.

(5) Litmus-Milk Culture

The strain does not show any ability of reducing the litmus and is free of coagulation, but has an ability of peptonization.

(6) Skimmed Milk-Acetate Agar Culture

The strain exhibits a strong proteolytic activity and grows while forming highly viscous gel-like masses on the agar plate.

3. Physiological Properties

Physiological properties of the WAP-8294 strain are as follows:

| | |
|---|---|
| (1) Reduction of Nitrate | − |
| (2) Denitrification Reaction | − |
| (3) MR Test | − |
| (4) VP Test | − |
| (5) Formation of Indole | − |
| (6) Formation of Hydrogen Sulfide | − |
| (7) Hydrolysis of Starch | − |
| (8) Use of Citric Acid | |
| ① Koser Culture Medium | − |
| ② Simmonds Culture Medium | − |
| ③ Christensen Culture Medium | + |
| (9) Use of Inorganic Nitrogen Source | |
| ① Sodium Nitrate | + |
| ② Ammonium Sulfate | + |
| ③ Sodium Glutamate | + |
| (10) Formation of Pigment | |
| ① King A Culture Medium | − |
| ② King B Culture Medium | − |
| (11) Urease | − |
| (12) Oxidase | + |
| (13) Catalase | + |
| (14) Growth Temperature | 15 to 37° C. |
| (15) Growth pH | 5 to 8 |
| (16) Behavior Against Oxygen | Aerobic |
| (17) O—F Test | non-decomposition type |
| (18) Deoxyribonuclease | + |
| (19) Phosphatase | + |
| (20) Hemolysis | β |
| (21) Degradation of Cellulose | − |
| (22) Degradation of Tween | |
| ① Tween 20 | + |
| ② Tween 40 | + |
| ③ Tween 60 | + |
| ④ Tween 80 | + |
| (23) Degradation of Colloidal Chitin | + |
| (24) Degradation of Polysaccharide | |
| ① CMC | + |
| ② Alginic Acid | − |
| ③ Pectic Acid | − |
| (25) Bacteriolytic Activity | |
| ① *Saccharomyces cerevisiae* | + |
| ② *Bacillus subthis* | + |
| ③ *Escherichia coli* | + |
| (26) GC Content | 68.3% (HPLC method) |

(27) Formation of Acid and Gas from Sugars

| Sugar | Formation of Acid (Peptone Water) | Formation of Gas (Bouillon-Agar) | Use of Sugar Davis Culture Medium) |
|---|---|---|---|
| L-Arabinose | − | − | − |
| D-Xylose | − | − | − |
| D-Glucose | + | − | − |
| D-Mannose | + | − | − |
| D-Fructose | + | − | − |
| D-Galactose | + | − | − |
| Maltose | + | − | + |
| Sucrose | + | − | − |
| Lactose | + | − | − |
| Trehalose | + | − | − |
| D-Sorbitol | − | − | − |
| D-Mannitol | − | − | − |
| Inositol | − | − | − |
| Glycerin | − | − | − |
| Starch | + | − | + |
| Cellobiose | + | − | + |

When the foregoing results concerning the WAP-8294 strain are compared with the details of bacterial species disclosed in Bergey's Manual of Systematic Bacteriology, Vol. 3 (1989), it can be concluded that the strain is a Gram-negative aerobic rod free of flagellum and has the motility through gliding and that the strain, therefore, belongs to Gliding Bacteria.

Gliding Bacteria are classified into Nonfruiting Gliding Bacteria which do not form any fruiting body and Fruiting Gliding Bacteria which form fruiting bodies. The strain does not form any fruiting body and therefore, belongs to Non-fruiting Gliding Bacteria. The Gliding Bacteria are further divided into three orders, i.e., *Cytophagales, Beggiatoles* and *Lysobacterales* which are clearly discriminated from one another on the basis of the GC content of each DNA which is one of important key characters. For this reason, the DNA of the strain was extracted by the usual method and, as a result, the GC content thereof is found to be a high level on the order of 68.3% as determined by the HPLC method disclosed in FEMS Microbiol. Letters, 1984, 25, p. 125. Accordingly, it can be concluded that the strain belongs to the genus *Lysobacter* of the order *Lysobacterales* which have a high GC content ranging from 65 to 71%.

When comparing the properties of the strain with those of species belonging to the same genus, the properties thereof are similar to those of *Lysobacter enzymogenes,* but are not in agreement with the latter in minute details such as the ability of assimilating citric acid. Accordingly, the strain is named *Lysobacter* sp. WAP-8294.

The WAP-8294 strain was deposited with National Institute of Bioscience and Human-Technology, Agency of Industrial Science & Technology, Ministry of International Trade and Industry, 1–3, higashi 1-chome, Tsukuba-shi, Ibaraki-ken 305, JAPAN on Jan. 31, 1994 under the accession number of FERM BP-4990 (FERM P-14093). Bacteria including *Lysobacter* quite easily undergo changes in their taxononic properties as the general nature thereof and the WAP-8294 strain is not an exception. However, all of the microorganisms having an ability of producing the antibiotic WAP-8294A including variants naturally mutated or those artificially mutated with a variety of mutagens may be used in the method of the present invention.

(Cultivation and Production)

The antibiotic WAP-8294A of the present invention is produced by inoculating a nutrient source-containing culture medium with the foregoing WAP-8294A-producing bacteria and aerobically cultivating the bacteria. When the antibiotic WAP-8294A-producing bacteria are cultivated, the bacteria use, for instance, assimilable organic carbon containing compounds such as glucose, fructose, starch, dextrin, glycerin, molasses, starch syrup, fats and oils and organic acids as carbon sources; and organic and inorganic nitrogen containing compounds such as soybean flour, cotton seed flour, corn steep liquor, casein, peptone, yeast extract, meat extract, germ, urea, amino acids and ammonium salts as nitrogen sources. In addition, examples of such salts are inorganic salts such as sodium, potassium, calcium and magnesium salts and phosphates which may be used alone or in any combination. Moreover, it is desirable to optionally add, to the culture medium, heavy metal salts such as iron salts, copper salts, zinc salts and cobalt salts; vitamins required for the growth of the microorganism such as biotin and vitamin $B_1$; and other organic and/or inorganic substances capable of promoting the growth of the antibiotic WAP-8294A-producing bacteria and improving the yield of the WAP-8294A. The culture medium may likewise comprise an anti-foaming agent such as silicone oil or a polyalkylene glycol ether and a surfactant.

The strain is cultured by any method commonly used for the production of antibiotics, but submerged aeration-agitation culture techniques are preferred for maintaining the aerobic conditions and the usual shaking culture in a flask is suitable for the laboratory culture. The cultivation may in general be performed at a temperature ranging from 20° to 40° C. and preferably 25° to 30° C. The cultivation is carried out at a pH ranging from about 6 to 8 and preferably about 7. The cultivation time ranging from about 2 to 6 days is sufficient for ensuring a desired yield of the WAP-8294A accumulated in the culture medium.

(Isolation and Purification)

The recovery of the antibiotic WAP-8294A thus accumulated in the culture medium may advantageously be carried out through the use of physicochemical properties of the antibiotic substances of the present invention as will be detailed later. More specifically, the antibiotic WAP-8294A is present in the filtrate of the culture medium and therefore, the filtrate of the culture medium is collected by first adding a filter aid such as Celite or Radiolite thereto and then removing the bacterial cells through filtration under reduced pressure or centrifugation.

The antibiotics WAP-8294A are considered to be water-soluble polypeptide antibiotics in the light of the physicochemical properties thereof detailed below and thus composed of relatively large compounds each having a molecular weight ranging from 1,400 to 1,700. When collecting the WAP-8294A from the filtrate of the culture medium while taking these properties into consideration, adsorbent resins such as Diaion HP-20, Sepabeads SP207, CHP-20 (available from Mitsubishi Chemical Industries Ltd.), Amberlite XAD-2 (available from Rohm & Haas Co.), Duolite S-30 (available from Diamond Shamrock Chemical Co.) and, in particular, the antibiotic is efficiently purified by active carbon column chromatography.

For instance, the filtrate of the culture medium having a pH of 6.9 is passed through a column packed with Amberlite IR-120B ($H^+$ type), the resulting acidic liquid passed through the column is then passed through a column packed with active carbon without any treatment to thus adsorb the filtrate, followed by water-washing and then elution with an 80% acetone-water mixture or an alkaline 80% acetone-water mixture as an elute to thus recover the antibiotic WAP-8294A. After distilling off the acetone from the eluate under reduced pressure, the residue obtained is extracted with ethyl acetate under an acidic condition to remove oil-soluble impurities and then the aqueous phase is again extracted with an organic solvent having high polarity such as n-butanol to recover the WAP-8294A. After distilling off the n-butanol from the extract at a low temperature, the residue per se is concentrated to dryness or a poor solvent is added to the concentrate of the residue to thus precipitate the WAP-8294A, followed by centrifugation or filtration under reduced pressure to give a crude substance.

The crude substance thus recovered can further be purified by countercurrent distribution methods represented by centrifugal liquid-liquid partition chromatography, adsorption chromatography such as silica gel column chromatography and partition chromatography such as cellulose column chromatography, which may be used alone or in combination, to give a highly purified substance, since the WAP-8294A can be extracted with a polar organic solvent such as n-butanol under an acidic condition.

Alternatively, it is also possible to purify the substance by making use of the molecular sieve effect of Sephadex G-10, G-15, LH-20 (available from Pharmacia Company) or Biogel P-4 Gel (available from Bio-Rad Laboratories) and then developing and eluting the substance with water, water-containing lower alcohols such as water-containing methanol, diluted alkali or acid aqueous solutions and aqueous solution containing appropriate salts which may be used alone or in combination.

The individual 7 components AX, $A_1$, $A_2$, $A_3$, $A_4$, $A_5$ and $A_6$ are obtained by further purifying and separating the WAP-8294A through, for instance, the countercurrent distribution techniques discussed above and/or high performance liquid chromatography techniques. The 13 kinds of components AX-1, AX-2, AX-3, AX-4, AX-5, AX-6, AX-7, AX-8, AX-9, AX-10, AX-11, AX-12 and AX-13 can likewise be obtained by purifying and separating the AX component in the manner similar to those used above.

Packing materials used in the high performance liquid chromatography may be silica gel, commercially available excellent carriers in which alkyl groups such as octadecyl and octyl groups are chemically bonded to the silanol groups of silica gel, or carriers for general purpose such as polystyrene type porous polymer gels. The WAP-8294A and the AX component can be separated into individual components through the use of these packing materials in high efficiency. The mobile phase usable in the high performance liquid chromatography may be water-containing acetonitrile acidified by, for instance, trifluoroacetic acid, water-containing lower alcohols such as water-containing methanol, and buffer solutions.

(Physicochemical Properties)

Physicochemical properties of the WAP-8294A, $A_1$, $A_2$, $A_4$, AX, AX-8, AX-9 and AX-13 obtained through the foregoing various chromatography techniques, substances which are obtained through complete acid-hydrolysis thereof and positive in the ninhydrin reaction, and ether extracts of the acid-hydrolyzates will be detailed below.

Antibiotic WAP-8294A (1) Appearance: white powder;

(2) Melting Point: 213°–220° C. (decomposed);

(3) Solubility: soluble in water, methanol, n-butanol, dimethylformamide and dimethylsulfoxide and insoluble in acetone, ethyl acetate and chloroform;

(4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;

(5) Retention Time in High Performance Liquid Chromatography (FIG. 1): 4.0 to 6.1 minutes, 8.0 minutes, 11.1 minutes, 12.5 minutes, 16.5 minutes, 17.9 minutes and 18.8 minutes;

(6) Ultraviolet Absorption Spectrum (in water): $\lambda_{max}$ : 275 nm, 280 nm, 287 nm;

(7) Infrared Absorption Spectrum (FT-IR, KBr): Characteristic Absorption Spectrum: 3300 $cm^{-1}$, 1720~1715 $cm^{-1}$, 1636 $cm^{-1}$, 1541 $cm^{-1}$, 1404 $cm^{-1}$, 1207 $cm^{-1}$, 1137 $cm^{-1}$;

(8) Molecular Weight: 1,400~1,700;

(9) Qualitative Test for Organic Compound (sodium-melting method): The antibiotic is a compound comprising carbon, hydrogen, oxygen and nitrogen elements;

(10) Acid-complete hydrolysis provides, as ninhydrin-positive substances, Asp, Glu, Gly, Leu, Ser, Trp, Orn, N-methylvaline, β-hydroxyaspartic acid and N-methylphenylalanine;

(11) Specific Rotation: $[\alpha]_D^{20}$=+42°(c=0.5, $H_2O$);

(12) Classification into Base, Acid and Neutral: Amphoteric.

Antibiotic WAP-8294$A_1$ (1) Appearance: white powder;

(2) Melting Point: 215°–225° C. (decomposed);

(3) Solubility: soluble in water, methanol, n-butanol, dimethylformamide and dimethylsulfoxide and insoluble in acetone, ethyl acetate and chloroform;

(4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;

(5) Retention Time in High Performance Liquid Chromatography: 8.0 minutes;

(6) Ultraviolet Absorption Spectrum (in water): $\lambda_{max}$: 275 nm, 280 nm, 287 nm;

(7) Infrared Absorption Spectrum (FT-IR, KBr): Characteristic Absorption Spectrum: 3300 $cm^{-1}$, 1720~1715 $cm^{-1}$, 1636 $cm^{-1}$, 1541 $cm^{-1}$, 1404 $cm^{-1}$, 1207 $cm^{-1}$, 1133 $cm^{-1}$;

(8) Molecular Weight: 1547.9 [FAB-MS m/z 1548.9 (M+H)$^+$, m/z 1546.7 (M-H)$^{-1}$];

(9) Molecular Formula: $C_{72}H_{109}O_{21}N_{17}$ measured m/z value of (M+H)$^+$ ion as determined by High Resolution FAB-Mass: 1548.8088; calculated m/z value: 1548.8063];

(10) Acid-complete hydrolysis provides Asp (1 mole), Glu (1 mole), Gly (1 mole), Leu (1 mole), Ser (2 mole), Trp (1 mole), Orn (2 mole), N-methylvaline (1 mole), β-hydroxyaspartic acid (1 mole), N-methylphenylalanine (1 mole) and 3-hydroxyoctanoic acid (1 mole);

(11) Specific Rotation: $[\alpha]_D^{20}$=+41°(c=0.5, $H_2O$);

(12) Classification into Base, Acid and Neutral: Amphoteric;

Antibiotic WAP-8294$A_2$ (1) Appearance: white powder;

(2) Melting Point: 215°–225° C. (decomposed);

(3) Solubility: soluble in water, methanol, n-butanol, dimethylformamide and dimethylsulfoxide and insoluble in acetone, ethyl acetate and chloroform;

(4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;

(5) Retention Time in High Performance Liquid Chromatography: 11.1 minutes;

(6) Ultraviolet Absorption Spectrum (in water) (FIG. 2): $\lambda_{max}$: 275 nm ($E_{1_{cm}}^{1\%}$ 31.8), 280 nm ($E_{1_{cm}}^{1\%}$ 33.4), 287 nm ($E_{1_{cm}}^{1\%}$ 29.2);

(7) Infrared Absorption Spectrum (FT-IR, KBr) (FIG. 3): Characteristic Absorption Spectrum: 3300 $cm^{-1}$, 1720~1715 $cm^{-1}$, 1636 $cm^{-1}$, 1541 $cm^{-1}$, 1404 $cm^{-1}$, 1207 $cm^{-1}$, 1137 $cm^{-1}$;

(8) $^1$H-NMR Spectrum: (270 MHz, $D_2O$) (FIG. 4): There are observed complicated proton signals originated from methyl, methylene, methine, and heterocycles or aromatic rings;

(9) Molecular Weight: 1561.9 [FAB-Mass m/z 1562.9 (M+H)$^+$, m/z 1561.2 (M-H)$^{-1}$];

(10) Molecular Formula: $C_{71}H_{111}O_{21}N_{17}$ [measured m/z value of (M+H)$^+$ ion as determined by High Resolution FAB-Mass: 1562.8224; calculated m/z value: 1562.8219];

(11) Acid-complete hydrolysis provides, as hydrolyzates, Asp (1 mole), Glu (1 mole), Gly (1 mole), Leu (1 mole), Ser (2 mole), Trp (1 mole), Orn (2 mole), N-methylvaline (1 mole),β-hydroxyaspartic acid (1 mole), N-methylphenylalanine (1 mole) and 3-hydroxy-7-methyloctanoic acid (1 mole);

(12) Specific Rotation: $[\alpha]_D^{20}=+42°(c=0.5, H_2O)$;

(13) Classification into Base, Acid and Neutral: Amphoteric;

Antibiotic WAP8294A, (1) Appearance: white powder;

(2) Melting Point: 215°–225° C. (decomposed);

(3) Solubility: soluble in water, methanol, n-butanol, dimethylformamide and dimethylsulfoxide and insoluble in acetone, ethyl acetate and chloroform;

(4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;

(5) Retention Time in High Performance Liquid Chromatography: 16.5 minutes;

(6) Ultraviolet Absorption Spectrum (in water): $\lambda_{max}$: 275 nm, 280 nm, 287 nm;

(7) Infrared Absorption Spectrum (FT-IR, KBr): Characteristic Absorption Spectrum: 3300 $cm^{-1}$, 1720–1715 $cm^{-1}$, 1636 $cm^{-1}$, 1541 $cm^{-1}$, 1404 $cm^{-1}$, 1207 $cm^{-1}$, 1137 $cm^{-1}$;

(8) Molecular Weight: 1575.9 [FAB-Mass m/z 1576.9 (M+H)$^+$, m/z 1575.4 (M-H)$^-$];

(9) Molecular Formula: $C_{74}H_{113}O_{21}N_{17}$ [measured m/z value of (M+H)$^+$ ion as determined by High Resolution FAB-Mass: 1576.8363; calculated m/z value: 1576.8375];

(10) Acid hydrolysis provides, as hydrolyzates, Asp (1 mole), Glu (1 mole), Gly (1 mole), Leu (1 mole), Ser (2 mole), Trp (1 mole), Orn (2 mole), N-methylvaline (1 mole), β-hydroxyaspartic acid (1 mole), N-methylphenylalanine (1 mole) and 3-hydroxy-8-methylnonanoic acid (1 mole);

(11) Specific Rotation: $[\alpha]_D^{20}=+43°(c=0.5, H_2O)$;

(12) Classification into Base, Acid and Neutral: Amphoteric.

The elution conditions for the $C_{18}$ reverse phase silica gel-high performance liquid chromatography of the antibiotics WAP-8294A, $A_1$, $A_2$ and $A_4$ are as follows:

Column: YMC A-312 (6×150 mm)

Mobile Phase: 0.05% trifluoroacetic acid-containing acetonitrile : water (45 : 55)

Detection Wavelength: UV 214 nm

Flow Rate: 1 ml/min

Antibiotic WAP-8294AX (1) Appearance: white powder;

(2) Melting Point: 196°–200° C. (decomposed);

(3) Solubility: soluble in water, methanol, n-butanol, dimethylformamide and dimethylsulfoxide and insoluble in acetone, ethyl acetate and chloroform;

(4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;

(5) Retention Time in High Performance Liquid Chromatography (FIG. 6): 5.3 minutes, 5.9 minutes, 6.2 minutes, 6.5 minutes, 6.9 minutes, 7.3 minutes, 8.1 minutes, 9.3 minutes, 9.8 minutes, 11.3 minutes, 12.1 minutes, 13.7 minutes and 15.0 minutes;

(6) Ultraviolet Absorption Spectrum (in water): $\lambda_{max}$: 273 nm, 280 nm, 289 nm;

(7) Infrared Absorption Spectrum (FT-IR, KBr): Characteristic Absorption Spectrum: 3300 $cm^{-1}$, 1720–1715 $cm^{-1}$, 1636 $cm^{-1}$, 1541 $cm^{-1}$, 1404 $cm^{-1}$, 1207 $cm^{-1}$, 1137 $cm^{-1}$;

(8) Molecular Weight: 1,400–1,700;

(9) Qualitative Test for Organic Compound (sodium-melting method): The antibiotic is a compound comprising carbon, hydrogen, oxygen and nitrogen elements;

(10) Acid-complete hydrolysis provides, as ninhydrin-positive substances and fatty acids, Asp, Glu, Gly, µ-Ala, Leu, Ser, Trp, Orn, Val, N-methylvaline, β-hydroxyaspartic acid, Phe, N-methylphenylalanine and 3-hydroxy-7-methyloctanoic acid;

(11) Specific Rotation: $[\alpha]_D^{20}=+24°(c=0.5, H_2O)$;

(12) Classification into Base, Acid and Neutral: Amphoteric;

Antibiotic WAP-8294AX-8

(1) Appearance: white powder;

(2) Melting Point: 196°–200° C. (decomposed);

(3) Solubility: soluble in water, methanol, n-butanol, dimethylformamide and dimethylsulfoxide and insoluble in acetone, ethyl acetate and chloroform;

(4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a. UV lamp; negative in Molisch, silver nitrate, ferric chloride and Dragendorff's reactions;

(5) Retention Time in High Performance Liquid Chromatography: 9.3 minutes;

(6) Ultraviolet Absorption Spectrum (in water) (FIG. 7): $\lambda_{max}$: 273 nm, 280 nm, 289 nm;

(7) Infrared Absorption Spectrum (FT-IR, KBr) (FIG. 8): Characteristic Absorption Spectrum: 3300 $cm^{-1}$, 1720–1715 $cm^{-1}$, 1636 $cm^{-1}$, 1541 $cm^{-1}$, 1404 $cm^{-1}$, 1207 $cm^{-1}$, 1133 $cm^{-1}$;

(8) $^1$H-NMR Spectrum: (270 MHz, DMSO-$D_6$) (FIG. 9): There are observed complicated proton signals originated from methyl, methylene, methine, and heterocycles or aromatic rings;

(9) Molecular Weight: 1543 [FAB-Mass m/z 1549 (M+H)$^+$];

(10) Molecular Formula: $C_{72}H_{109}O_{21}N_{17}$ [measured m/z value of (M+H)$^+$ ion as determined by High Resolution FAB-Mass: 1548.8079; calculated m/z value: 1548.8063];

(11) Acid-complete hydrolysis provides, as hydrolyzates, Asp (1 mole), Glu (1 mole), Gly (1 mole), Leu (1 mole), Ser (2 mole), Trp (1 mole), Orn (2 mole), Val (1 mole), β-hydroxyaspartic acid (1 mole), N-methylphenylalanine (1 mole) and 3-hydroxy-7-methyloctanoic acid (1 mole);

(12) Specific Rotation: $[\alpha]_D^{20}=+25°(c=0.5, H_2O)$;

(13) Classification into Base, Acid and Neutral: Amphoteric;

Antibiotic WAP-8294AX-9

(1) Appearance: white powder;
(2) Melting Point: 216°–220° C. (decomposed);
(3) Solubility: soluble in water, methanol, n-butanol, dimethylformamide and dimethylsulfoxide and insoluble in acetone, ethyl acetate and chloroform;
(4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;
(5) Retention Time in High Performance Liquid Chromatography: 9.8 minutes;
(6) Ultraviolet Absorption Spectrum (in water):
$\lambda_{max}$ : 273 nm, 280 nm, 289 nm;
(7) Infrared Absorption Spectrum (FT-IR, KBr): Characteristic Absorption Spectrum: 3300 $cm^{-1}$, 1720–1715 $cm^{-1}$, 1636 $cm^{-1}$, 1541 $cm^{-1}$, 1404 $cm^{-1}$, 1207 $cm^{-1}$, 1137 $cm^{-1}$;
(8) Molecular Weight: 1548 [FAB-Mass m/z 1549 $(M+H)^+$; m/z 1547 $(M-H)^-$];
(9) Molecular Formula: $C_{72}H_{109}O_{21}N_{17}$ [measured m/z value of $(M+H)^+$ ion as determined by High Resolution FAB-Mass: 1548.8065; calculated m/z value: 1548.8063];
(10) Acid-complete hydrolysis provides, as hydrolyzates, Asp (1 mole), Glu (1 mole), Gly (1 mole), Leu (1 mole), Ser (2 mole), Trp (1 mole), Orn (2 mole), N-methylvaline (1 mole), β-hydroxyaspartic acid (1 mole), Phe (1 mole) and 3-hydroxy-7-methyloctanoic acid (1 mole);
(11) Specific Rotation: $[\alpha]_D^{20}$=+28°(c=0.5, $H_2O$);
(12) Classification into Base, Acid and Neutral: Amphoteric;

Antibiotic WAP-8294AX-13

(1) Appearance: white powder;
(2) Melting Point: 205°–210° C. (decomposed);
(3) Solubility: soluble in water, methanol, n-butanol, dimethylformamide and dimethylsulfoxide and insoluble in acetone, ethyl acetate and chloroform;
(4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;
(5) Retention Time in High Performance Liquid Chromatography: 15.0 minutes;
(6) Ultraviolet Absorption Spectrum (in water):
$\lambda_{max}$ : 273 nm, 280 nm, 289 nm;
(7) Infrared Absorption Spectrum (FT-IR, KBr): Characteristic Absorption Spectrum: 3300 $cm^{-1}$, 1720–1715 $cm^{-1}$, 1636 $cm^{-1}$, 1541 $cm^{-1}$, 1404 $cm^{-1}$, 1207 $cm^{-1}$, 1137 $cm^{-1}$;
(8) Molecular Weight: 1576 [FAB-Mass m/z 1577 $(M+H)^+$];
(9) Molecular Formula: $C_{74}H_{113}O_{21}N_{17}$ [measured m/z value of $(M+H)^+$ ion as determined by High Resolution FAB-Mass: 1576.8324; calculated m/z value: 1576.8375];
(10) Acid-complete hydrolysis provides, as hydrolyzates, Asp (1 mole), Glu (1 mole), β-Ala (1 mole), Leu (1 mole), Ser (2 mole), Trp (1 mole), Orn (2 mole), N-methylvaline (1 mole), β-hydroxyaspartic acid (1 mole), N-methylphenylalanine (1 mole) and 3-hydroxy-7-methyloctanoic acid (1 mole);
(11) Specific Rotation: $[\alpha]_D^{20}$=+27°(c=0.5, $H_2O$);
(12) Classification into Base, Acid and Neutral: Amphoteric;

The elution conditions for the $C_{18}$ reverse phase silica gel-high performance liquid chromatography of the antibiotics WAP-8294AX, AX-8, AX-9 and AX-13 are as follows:

Column: YMC A-312 (6×150 mm)
Mobile Phase: 0.05% trifluoroacetic acid-containing acetonitrile : water (37 : 63)
Detection Wavelength: UV 214 nm
Flow Rate: 1 ml/min (Biological Properties)
(1) Antibacterial Activity Table 4 shows the results of the inspection of the WAP-8294A, $A_1$, $A_2$ and $A_4$ for the antibacterial activity. The determination of the minimum inhibitory concentration (MIC) was carried out by broth dilution method which made use of a sensitive bouillon medium (available from Eiken Chemical Co., Ltd.).

The data shown in Table 4 clearly indicate that the WAP-8294A, $A_1$, $A_2$ and $A_4$ exhibited strong antibacterial activity against Gram-positive bacteria including MRSA (methicillin-resistant *Staphylococcus aureus*) and the activity is characterized in that it is increased to not less than 8 times that observed in the foregoing culture medium when 10% bovine serum is added to the culture medium.

On the other hand, they do not show any activity against Gram-negative bacteria, fungi and yeast.

TABLE 4-1

| | MIC (μg/ml) | | | |
|---|---|---|---|---|
| | A | | $A_1$ | |
| | Addition of Serum | | | |
| Bacterium Tested | None | 10% | None | 10% |
| *Staphylococcus aureus* No. 1 (MRSA clinically isolated strain) | 0.78 | <0.10 | 0.39 | <0.10 |
| *Staphylococcus aureus* No. 11 (MRSA clinically isolated strain) | 0.78 | <0.10 | 0.39 | <0.10 |
| *Staphylococcus aureus* 371 R (MRSA clinically isolated strain) | 0.78 | <0.10 | 0.39 | <0.10 |

TABLE 4-1-continued

| | MIC (μg/ml) | | | |
|---|---|---|---|---|
| | A | | $A_1$ | |
| | Addition of Serum | | | |
| Bacterium Tested | None | 10% | None | 10% |
| Staphylococcus aureus (ATCC 25923) | 0.78 | <0.10 | 0.39 | <0.10 |
| Staphylococcus epidermidis (ATCC 12228) | 0.78 | <0.10 | 0.39 | <0.10 |
| Staphylococcus pyogenes (ATCC 19615) | 6.25 | 25 | 6.25 | 25 |
| Bacillus subtilis (ATCC 6633) | 0.78 | <0.10 | 0.39 | <0.10 |
| Escherichia coli (ATCC 25922) | >100 | >100 | >100 | >100 |
| Pseudomonas aeruginosa (ATCC 9027) | >100 | >100 | >100 | >100 |
| Candida albicans (TIMM 0239) | >100 | >100 | >100 | >100 |
| Aspergillus fumigatus (IAM 2004) | >100 | >100 | >100 | >100 |

TABLE 4-2

| | MIC (μg/ml) | | | |
|---|---|---|---|---|
| | $A_2$ | | $A_4$ | |
| | Addition of Serum | | | |
| Bacterium Tested | None | 10% | None | 10% |
| Staphylococcus aureus No. 1 (MRSA clinically isolated strain) | 0.78 | <0.10 | 0.78 | <0.10 |
| Staphylococcus aureus No. 11 (MRSA clinically isolated strain) | 0.78 | <0.10 | 0.78 | <0.10 |
| Staphylococcus aureus 371 R (MRSA clinically isolated strain) | 0.78 | <0.10 | 0.78 | <0.10 |
| Staphylococcus aureus (ATCC 25923) | 0.78 | <0.10 | 0.78 | <0.10 |
| Staphylococcus epidermidis (ATCC 12228) | 0.78 | <0.10 | 0.78 | <0.10 |
| Streptococcus pyogenes (ATCC 19615) | 6.25 | 25 | 6.25 | 25 |
| Bacillus subtilis (ATCC 6633) | 0.78 | <0.10 | 0.78 | <0.10 |
| Escherichia coli (ATCC 25922) | >100 | >100 | >100 | >100 |
| Pseudomonas aeruginosa (ATCC 9027) | >100 | >100 | >100 | >100 |
| Candida albicans (TIMM 0239) | >100 | >100 | >100 | >100 |
| Aspergillus fumigatus (IAM 2004) | >100 | >100 | >100 | >100 |

The antibacterial activities of the antibiotics WAP-8294AX, AX-8, AX-9 and AX-13 were likewise determined. The results are listed in Table 5. The determination of the minimum inhibitory concentration (MIC) thereof was carried out by broth dilution method using Muller-Hinton broth (available from DIFCO Company) supplemented with 2% sodium chloride for MRSA and Muller-Hinton broth per se for other bacteria.

The data shown in Table 5 indicate that the antibiotics WAP-8294AX, AX-8, AX-9 and AX-13 exhibited strong antibacterial activity against Gram-positive bacteria including methicillin-resistant Staphylococcus aureus and it is found that the activity is increased to about 2 times that observed in the foregoing culture medium when 10% bovine serum is added to the culture medium.

On the other hand, they do not show any activity against Gram-negative bacteria, fungi and yeast.

TABLE 5-1

| | MIC (μg/ml) | | | |
|---|---|---|---|---|
| | AX | | AX-8 | |
| | Addition of Serum | | | |
| Bacterium Tested | None | 10% | None | 10% |
| Staphylococcus aureus No. 1 (MRSA clinically isolated strain) | 1.56 | 0.78 | 3.13 | 3.13 |
| Staphylococcus aureus (ATCC 25923) | 1.56 | 0.78 | 3.13 | 1.56 |
| Staphylococcus epidermidis (ATCC 12228) | 1.56 | 0.78 | 1.56 | 0.78 |
| Streptococcus pyogenes (ATCC 19615) | >100 | >100 | >100 | >100 |
| Bacillus subtilis (ATCC 6633) | 1.56 | 0.78 | 1.56 | 0.78 |
| Escherichia coli (ATCC 25922) | >100 | >100 | >100 | >100 |

TABLE 5-1-continued

|  | MIC (μg/ml) | | | |
|---|---|---|---|---|
|  | AX | | AX-8 | |
|  | Addition of Serum | | | |
| Bacterium Tested | None | 10% | None | 10% |
| Pseudomonas aeruginosa (ATCC 9027) | >100 | >100 | >100 | >100 |
| Candida albicans (TIMM 0239) | >100 | >100 | >100 | >100 |
| Aspergillus fumigatus (IAM 2004) | >100 | >100 | >100 | >100 |

TABLE 5-2

|  | MIC (μg/ml) | | | |
|---|---|---|---|---|
|  | AX-9 | | AX-13 | |
|  | Addition of Serum | | | |
| Bacterium Tested | None | 10% | None | 10% |
| Staphylococcus aureus No. 1 (MRSA clinically isolated strain) | 3.13 | 1.56 | 3.13 | 3.13 |
| Staphylococcus aureus (ATCC 25923) | 3.13 | 1.56 | 3.13 | 3.13 |
| Staphylococcus epidermidis (ATCC 12228) | 1.56 | 0.78 | 1.56 | 0.78 |
| Streptococcus pyogenes (ATCC 19615) | >100 | >100 | >100 | >100 |
| Bacillus subtilis (ATCC 6633) | 3.13 | 1.56 | 3.13 | 1.56 |
| Escherichia coli (ATCC 25922) | >100 | >100 | >100 | >100 |
| Pseudomonas aeruginosa (ATCC 9027) | >100 | >100 | >100 | >100 |
| Candida albicans (TIMM 0239) | >100 | >100 | >100 | >100 |
| Aspergillus fumigatus (IAM 2004) | >100 | >100 | >100 | >100 |

(2) Protective Effect Of WAP-8294A Against Experimental MRSA Infection In Mice

Since the antibiotic WAP-8294A shows a strong antibacterial activity against Gram-positive bacteria including MRSA as seen from the in vitro antibacterial activity thereof as shown in Table 4, a test for protecting mice from infection with Staphylococcus aureus No. 1 (a clinically isolated strain of MRSA) was carried out.

The experiments were carried out by intra-peritoneally administering 0.5 mg/0.5 ml/mouse of cyclophosphamide to ICR-MCH mice [4-week-old male mice (available from Nippon CLEA Co., Ltd.), 8 animals per group] 3 days before the infection and then infecting the animals through intra-peritoneal administration of 0.5 ml each of a liquid containing $2 \times 10^6$/ml of Staphylococcus aureus No. 1 strain supplemented with 5% mucin. One hour after the infection, 10 mg/kg of Vancomycin HCl (available from Shionogi & Co., Ltd.) and 0.2 ml/mouse of the antibiotic WAP-8294A (containing 10 mg/kg, 5 mg/kg, 2.5 mg/kg, 1.0 mg/kg, 0.5 mg/kg, 0.25 mg/kg, 0.1 mg/kg or 0.05 mg/kg of the antibiotic) was once subcutaneously injected to mice. To control groups, there was subcutaneously administered 0.2 ml each of physiological saline.

As will be seen from the results of these experiments shown in Table 6 given below, all of the control animals free of any treatment died within 3 days after the infection. On the other hand, as to the antibiotic-administered group, 5 animals out of 8 animals to which 10 mg/kg of Vancomycin had been administered were survived even 5 days after the infection. Contrary to this, the WAP-8294A showed an excellent therapeutic effect at a low dose level as seen from the results listed in Table 6. The $ED_{50}$ value thereof was determined by the probit method and was found to be 0.155 mg/kg.

TABLE 6

Results of WAP-8294A Treatment of Experimental Systemic MRSA in Infection in Mice

| Test Group | Dose (mg/kg) | Survival/ No. of Test Animals |
|---|---|---|
| Control (physiological saline) |  | 0/8 |
| Vancomycin | 10 | 5/8 |
| Antibiotic WAP-8294A | 10 | 8/8 |
|  | 5 | 8/8 |
|  | 2.5 | 8/8 |
|  | 1.0 | 8/8 |
|  | 0.5 | 7/8 |
|  | 0.25 | 5/8 |
|  | 0.10 | 3/8 |
|  | 0.05 | 1/8 |

Since the antibiotic WAP-8294AX shows strong antibacterial activity against Gram-positive bacteria including MRSA as seen from the in vitro antibacterial activity thereof as shown in Table 5, a test for protecting mice from infection with Staphylococcus aureus JCM8702 (a clinically isolated strain of MRSA) was carried out.

The experiments were carried out by intra-peritoneally administering 0.5 mg/0.5 ml/mouse of cyclophosphamide to ICR-MCH mice [4-week-old male mice (available from Nippon CLEA Co., Ltd.), 8 animals per group] 3 days before the infection and then infecting the animals through intra-peritoneal administration of 0.5 ml each of a liquid containing $2 \times 10^4$/ml of Staphylococcus aureus JCM8702 strain supplemented with 5% mucin. One hour after the infection, 10 mg/kg of Vancomycin HCl (available from Shionogi & Co., Ltd.) and 0.2 ml/mouse of the antibiotic WAP-8294AX (containing 10 mg/kg, 2.5 mg/kg, 1.0 mg/kg or 0.5 mg/kg of the antibiotic) was once subcutaneously injected to mice. To control groups, there was subcutaneously administered 0.2 ml each of physiological saline.

As will be seen from the results of these experiments shown in Table 7 given below, 6 animals out of 8 control animals free of any treatment died within 3 days after the infection. On the other hand, as to the antibiotic-administered group, 5 animals out of 8 animals to which 10 mg/kg of Vancomycin had been administered were survived even 5 days after the infection. Contrary to this, the WAP-8294AX showed an excellent therapeutic effect at a low dose level as seen from the results listed in Table 7. The $ED_{50}$ value thereof was determined by the probit method and was found to be 1.25 mg/kg.

TABLE 7

Results of WAP-8294A Treatment of Experimental Systemic MRSA Infection in Mice

| Test Group | Dose (mg/kg) | Survival/ No. of Test Animals |
| --- | --- | --- |
| Control (physiological saline) | | 2/8 |
| Vancomycin | 10 | 5/8 |
| Antibiotic WAP-8294A | 10 | 7/8 |
| | 2.5 | 5/8 |
| | 1.0 | 4/8 |
| | 0.5 | 2/8 |

(3) Acute Toxicity Test in Mice

The antibiotic WAP-8294A was intravenously administered to mice (4-week-old ICR-MCH male mice; 5 animals per group) at a dose of 25 mg/kg, 50 mg/kg, 100 mg/kg or 250 mg/kg, but any acute toxicity was not observed.

The antibiotic WAP-8294AX was intraperitoneally administered to mice (4-week-old ICR-MCH male mice; 5 animals per group) at a dose of 25 mg/kg or 100 mg/kg, but any acute toxicity was not observed.

From the foregoing, the antibiotics WAP-8294A, $A_1$, $A_2$, $A_3$, $A_4$, $A_5$, $A_6$, AX, AX-1, AX-2, AX-3, AX-4, AX-5, AX-6, AX-7, AX-8, AX-9, AX-10, AX-11, AX-12 and AX-13 are found to be effective as therapeutic agent for treating bacterial infectious diseases, in particular, the infectious disease developed by infection with methicillin-resistant *Staphylococcus aureus*, in man and animals.

(Applications)

If the novel antibiotics of the present invention are administered as medicines, they may be administered in various dosage forms according to the usual manner. For instance, they may be used in the orally administrable forms such as powder, granules, tablets, capsules and syrup and may be used in the parenterally administrable forms such as (intravenous, intramuscular, subcutaneous) injections, drops, suppositories, paints and ointments, with safety. Moreover, the novel antibiotics of the present invention can likewise be used in the field of ophthalmic remedies in the parenterally administrable dosage forms such as eye drops and eye ointments, with safety, while taking into consideration their bactericidal rate faster than that of Vancomycin and their effectiveness at low concentrations.

These various pharmaceutical preparations may be prepared by the usual method, i.e., by incorporating, into the principal ingredient, pharmaceutically acceptable and currently used known auxiliary agents such as excipients, binders, disintegrators, coating agents, lubricants, stabilizers, corrigents or flavorings, solubilizing agents, suspending agents and diluents and then forming the mixture into a desired dosage form.

The dose thereof may vary depending on, for instance, diseases to be treated, routes of administration and dogage time, but they are preferably administered in a dose ranging from 5 mg to 2000 mg per day for adults which may be administered one time or in portions over several times.

The present invention will hereunder be described in more detail with reference to the following Examples, but the present invention is not restricted to these specific Examples.

EXAMPLE 1

To each of four 500 ml volume Erlenmeyer flasks, there was added 100 ml of a culture medium (pH 7.2) containing 2.5% glucose, 2.0% defatted soybean flour, 0.4% soybean oil, 0.25% sodium chloride and 0.5% calcium carbonate followed by sterilization, inoculation of these culture medium with one platinum loop each of Lysobacter sp. WAP-8294 strain cultivated in a slant agar medium and cultivation thereof at 30° C. for 2 days while reciprocating the flasks in a rotary shaker at 180 strokes/min. Then 500 ml volume Erlenmeyer flasks (the number of 150) to which 100 ml each of the foregoing culture medium was added and which were then sterilized were prepared, followed by inoculation thereof with 2 ml each of the culture medium and cultivation at 30° C. for 4 days while reciprocating the flasks in a rotary shaker at 180 strokes/min. The antibacterial activity was determined by the agar plate method using *Staphylococcus aureus* No. 1.

EXAMPLE 2

The culture media obtained in Example 1 were subjected to continuous centrifugation (9,000 rpm) to give 152 of supernatant. The supernatant (pH 6.9) was loaded on a column packed with Amberlite IR-120B ($H^+$ type, 1.5 l, available from Rohm & Haas Co.) to collect 15 l of an effluent and 3 l of an aqueous wash liquid. After combining the effluent and the wash liquid and adjusting the pH thereof to 3, the combined liquid was chromatographed by loading it on a column packed with active carbon (700 ml, available from Wako Pure Chemical Co., Ltd.). After washing with 4 l of water, active substances were eluted with 4 l of 80% acetone-water and 4 of 80% acetone-water (pH 12). The resulting eluate was concentrated to 800 ml, followed by adjustment of pH to 3 with hydrochloric acid and extraction with ethyl acetate (400 ml×3) and then with n-butanol (400 ml×3), concentration of the butanol phase and lyophilization thereof to give 6.4 g of a crude product (hydrochloride).

EXAMPLE 3

The crude substance (6.4 g) obtained in Example 2 was chromatographed by loading it on a column packed with cellulose (450 ml, available from E. Merck Company) and eluting and fractionating with a solvent system: acetonitrile-acetic acid-water (75: 1: 25). The active fractions were collected, concentrated and then lyophilized to give 880 mg of the WAP-8294A (hydrochloride) as white powder.

EXAMPLE 4

The WAP-8294A (700 mg) obtained in Example 3 was loaded on a reverse phase high performance liquid chromatography column packed with octadecyl silica gel [column: YMC-GEL SH-343-5, 20×250 mm, available from Yamamura Chemical Research Laboratory; mobile phase: 0.05% trifluoroacetic acid-containing acetonitrile-water (45 : 55)] in ten-odd portions to collect fractions containing WAP- 8294A$_1$, A$_2$ and A$_4$, followed by concentrating each fraction to give WAP-8294A$_1$ (50 mg), A$_2$ (210 mg) and A$_4$ (16 mg) as white powder (hydrochloride).

EXAMPLE 5

Amino Acid Analysis of WAP-8294A

The WAP-8294A (5 mg) obtained in Example 3 were dissolved in 0.5 ml of 4N methanesulfonic acid solution to which 0.2% 3-(2-aminomethyl)indole was added to completely hydrolyze the antibiotic with the acid at 110° C. for 24 hours. The resulting hydrolyzate was concentrated to dryness, dissolved in a small amount of water, followed by loading the solution on a column packed with Dowex 50WX-8 (H$^+$ type, 1 ml, available from Dow Chemical Company), washing with 20 ml of water and then eluting with 20 ml of a 0.5N NH, OH solution. The eluate was concentrated to dryness, dissolved in a small amount of water, then subjected to two-dimensional thin-layer chromatography [Cellulose plate; solvent 1: n-butanol: acetic acid: water (4: 1: 2); solvent 2: n-butanol: pyridine: acetic acid: water (15: 10: 3: 12)] and amino acid analysis (Hitachi Amino Acid Analyzer L-8500) and thus it was found that the eluate comprised Asp (1 mole), Glu (1 mole), Gly (1 mole), Ser (2 moles), Leu (1 mole), Trp (1 mole) and Orn (2 moles) as well as three kinds of unknown amino acids. The results of this two-dimensional TLC analysis of the antibiotic WAP-8294A is shown in FIG. 5.

EXAMPLE 6

Identification of Unknown Amino Acids

To 100 mg of the WAP-8294A obtained in Example 3, there was added 10 ml of a 6N HCl solution containing 4% thioglycollic acid followed by hydrolysis of the antibiotic at 110° C. for 20 hours. After concentrating the hydrolyzate, the pH thereof was adjusted to 7.0 and subjected to column chromatography using Sepabeads SP207 (available from Mitsubishi Chemical Industries, Ltd.) while developing with water. The fraction eluted from the column between 18 ml and 27 ml and containing unknown amino acid-1 was concentrated and loaded on a column packed with Dowex 50WX-8 (H$^+$ type, 9 ml). After eluting with a 0.1N HCl solution, the resulting eluate was concentrated to dryness to give 4 mg of unknown amino acid-1 hydrochloride as white powder. The amino acid was found to have a molecular weight of 149 [FAB-MS m/z: 150 (M+H)$^+$] and $^1$H-NMR spectrum [D$_2$O, 270 MHz; chemical shift: δ (ppm)] at 4.53 (1H, d, J=2.9 Hz) and 5.00 (1H, d, J=2.9 Hz) and thus supported to be β-hydroxyaspartic acid.

When comparing it with authentic sample of β-hydroxyaspartic acid hydrochloride (available from Sigma Company), the $^1$H-NMR spectra (chemical shifts) and the Rf value (0.20) observed on the cellulose TLC [solvent: n-butanol: pyridine: acetic acid: water (15: 10: 3: 12)] of the unknown amino acid-1 hydrochloride were completely identical to those observed for the authentic sample and accordingly, the unknown amino acid-1 was identified to be β-hydroxyaspartic acid.

Moreover, the fraction eluted form the Sepabeads SP207column between 30 ml and 45 ml and containing unknown amino acid-2 was concentrated and loaded on a column packed with 10 ml of active carbon. The fraction eluted between 24 and 34 ml was collected, loaded on a Dowex 50WX-8 column (1 ml), eluted with a 0.5N NH$_4$OH solution, followed by concentration to dryness to give 2.1 mg of the unknown amino acid-2 as white powder. This amino acid was found to have a molecular weight of 131 [FAB-MS m/z: 132 (M+H)$^+$] and $^1$H-NMR spectrum [D$_2$O, 270 MHz; chemical shift: δ (ppm)] at 1.18 (6H, dd, J=7.0 Hz), 2.38 (1H, dq, J=4.8, 7.0 Hz), 2.87 (3H, s) and 3.55 (1H, d, J=4.8 Hz) and thus presumed to be N-methylvaline. Thus, this amino acid was compared with authentic sample of N-methyl-DL-valine (available from Sigma Company) and it was found that the $^1$H-NMR spectra (chemical shifts) and the Rf value (0.71) observed on the cellulose TLC [solvent: n-butanol: pyridine: acetic acid: water (15: 10: 3: 12)] of the unknown amino acid-2 were completely identical to those observed for the authentic sample and accordingly, the unknown amino acid-2 was identified to be N-methylvaline.

Further the fraction eluted with 80% acetone from the Sepabeads SP207 column and containing unknown amino acid-3 was concentrated and loaded on a Dowex 50WX-8 column (H$^+$ type, 1 ml). After the elution thereof with a 1N HCl solution, the resulting eluate was concentrated to dryness to give 3.5 mg of unknown amino acid-3 hydrochloride as white powder. This amino acid was found to have a molecular weight of 179 [FAB-MS m/z: 180 (M+H)$^+$] and $^1$H-NMR spectrum [D$_2$O, 270 MHz; chemical shift: δ (ppm)] at 2.78 (1H, s), 3.32 (2H, d, J=6.2 Hz), 3.95 (1H, t, J=6.2 Hz), 7.4~7.5 (5H, m) and thus presumed to be N-methylphenylalanine. Thus, this amino acid was compared with authentic sample of N-methyl-L-phenylalanine (available from Sigma Company) and it was found that the $^1$H-NMR spectra (chemical shifts) and the Rf value (0.82) observed on the cellulose TLC [solvent: n-butanol: pyridine: acetic acid: water (15: 10: 3: 12)] of the unknown amino acid-3 were completely identical to those observed for the authentic sample and accordingly, the unknown amino acid-3 was identified to be N-methylphenylalanine.

EXAMPLE 7

Amino Acid Analysis of WAP-8294A$_1$, A$_2$ and A$_4$

About 30 μg of the WAP-8294A$_1$, A$_2$ or A$_4$ obtained in Example 4 was completely hydrolyzed with a 6N HCl solution at 110° C. for 24 hours, then concentrated and subjected to amino acid analysis. As a result, it was found that each of them comprised Asp (1 mole), Glu (1 mole), Gly (1 mole), Ser (2 moles), Leu (1 mole), Orn (2 moles), Trp (1 mole), β hydroxyaspartic acid (1 mole), N-methylvaline (1 mole) and N-methylphenylalanine (1 mole).

EXAMPLE 8

Isolation of Fatty Acids Constituting WAP-8294A$_1$, A$_2$ and A$_4$ and Structure Thereof The WAP-8294A$_1$ (10 mg) obtained in Example 4 was hydrolyzed with 6N HCl at 110° C. for 2 hours. The resulting hydrolyzate was extracted with ether, followed by concentration of the ether phase to dryness to give 0.8 mg of white powder. This substance was found to have a molecular weight of 160 [FAB-MS m/z: 161 (M+H)$^+$] and $^1$H-NMR spectrum [CDCl$_3$, 270 MHz; chemical shift: δ (ppm)] at 0.89 (3H, t, J=7.0 Hz), 1.3~1.55 (8H, m), 2.46 (1H, dd, J=16.5, 8.8 Hz), 2.58 (1H, dd, J=16.5, 3.3 Hz) and 4.03 (1H, m) and thus supported to be 3-hydroxyoctanoic acid. This substance (100 μg) was dissolved in 0.1 ml of benzene: methanol (8: 2) and converted into the methyl ester thereof at room temperature for 10 minutes by addition of a drop of trimethylsilyl diazomethane (available from Tokyo Chemical Industry Co., Ltd.). When the methyl ester derivative was subjected to EI-MS measurement, there were observed an ion peak at m/z of 173 (M$^+$ −1), fragment ion peaks at 156 (M$^+$ −18), 143 (M$^+$ −31) and 125 (M$^+$ −31 −18) and a characteristic base fragment ion peak at m/z of 103 originated from the cleavage of $C_3$–$C_4$ of 3-hydroxyfatty acid methyl ester and this substance was accordingly identified to be 3-hydroxyoctanoic acid.

The WAP-8294A$_2$ (10 mg) was hydrolyzed with an acid in the same manner used above, followed by extraction with ether and concentration of the ether phase to dryness to give 0.9 mg of white powder. This substance was found to have a molecular weight of 174 [FAB-MS m/z: 175 (M+H)$^+$] and $^1$H-NMR spectrum [CDCl$_3$, 270 MHz; chemical shift: δ (ppm)] at 0.87 (6H, d, J=6.6 Hz), 1.15~1.56 (7H, m), 2.50 (1H, dd, J=16.5, 8.8 Hz), 2.60 (1H, dd, J=16.5, 3.3 Hz) and 4.03 (1H, m) and the methyl ester derivative thereof showed EI-MS peaks at m/z of 187 (M$^+$ −1), 170 (M$^+$ −18), 157 (M$^+$ −31), 139 (M$^+$ −31 −18) and 103 (base fragment ion peak originated from the cleavage of $C_3$–$C_4$). This substance was accordingly identified to be 3-hydroxy-7-methyloctanoic acid.

The WAP-8294A$_4$ (10 mg) was hydrolyzed with an acid in the same manner used above, followed by extraction with ether and concentration of the ether phase to dryness to give 0.8 mg of white powder. This substance was found to have a molecular weight of 188 [FAB-MS m/z: 189 (M+H)$^+$] and $^1$H-NMR spectrum [CDCl$_3$, 270 MHz; chemical shift: δ (ppm)] at 0.80 (6H, d, J=6.8 Hz), 1.15~1.6 (9H, m), 2.43 (1H, dd, J=16.5, 8.8 Hz), 2.50 (1H, dd, J=16.5, 3.3 Hz) and 3.95 (1H, m) and the methyl ester derivative thereof showed EI-MS peaks at m/z of 201 (M$^+$ −1), 184 (M$^+$ −18), 171 (M$^+$ −31), 153 (M$^+$ −31 −18) and 103 (base fragment ion peak originated from the cleavage of $C_3$–$C_4$). This substance was accordingly identified to be 3-hydroxy-8-methylnonanoic acid.

EXAMPLE 9

A crude substance (9.0 g) obtained in the same manner used in Example 2 was chromatographed by loading it on a column packed with octadecyl silica gel (Chromatolex ODS-DM1020T available from Fuji Silisia Chemical Co., Ltd., 450 ml) and then eluted and fractionated with a 0.05% trifluoroacetic acid-containing acetonitrile: water (4 : 6) solvent system. The active fractions were collected, concentrated, then lyophilized to give 450 mg of the WAP-8294AX (hydrochloride) as white powder.

EXAMPLE 10

The WAP-8294AX (120 mg) obtained in Example 9 was loaded, in ten-odd portions, on a column packed with octadecyl silica gel for high performance liquid chromatography [column: YMC-GEL SH-343-5, 20×250 mm, available from Yamamura Chemical Research Laboratory; mobile phase: 0.05% trifluoroacetic acid-containing acetonitrile-water (37: 63)] in ten-odd portions to collect fractions each containing WAP-8294AX-8, AX-9 or AX-13, followed by concentration of each fraction to give the WAP-8294AX-8 (14 mg), AX-9 (10 mg) or AX-13 (12 mg) as white powder (hydrochloride).

EXAMPLE 11

Amino Acid Analysis of WAP-8294AX-8, AX-9, AX-13

The WAP-8294AX-8 (5 mg) obtained in Example 10 was dissolved in 0.5 ml of a 4N methanesulfonic acid solution supplemented with 0.2% 3-(2-aminomethyl)indole to carry out acid-complete hydrolysis thereof at 110° C. for 24 hours. Then the resulting hydrolyzate was concentrated to dryness, dissolved in a small amount of water, followed by loading on a column packed with Dowex 50WX-8 (H$^+$ type, available from Dow Chemical Company, 1 ml), washing with 20 ml of water and elution with 20 ml of 0.5N NH$_4$OH. The resulting eluate was concentrated to dryness, dissolved in a small amount of water and then subjected to two-dimensional thin layer chromatography [developing solvent for first dimension: n-butanol : acetic acid: water (4 : 1 : 2); developing solvent for secondary dimension: n-butanol: pyridine: acetic acid: water (15: 10 : 3 : 12)] and to amino acid analysis (Hitachi Amino Acid Analyzer L-8500). As a result, it was found that the WAP-8294AX-8 comprised Asp (1 mole), Glu (1 mole), Gly (1 mole), Ser (2 moles), Leu (1 mole), Trp (1 mole), Orn (2 moles), Val (1 mole), N-methylphenylalanine (1 mole) and β-hydroxyaspartic acid (1 mole).

Moreover, 5 mg each of the WAP-8294AX-9 and AX-13 were subjected to acid-complete hydrolysis and then the resulting hydrolyzates were subjected to amino acid analysis, in the same manner used above. As a result, it was found that the WAP-8294AX-9 comprised Asp (1 mole), Glu (1 mole), Gly (1 mole), Ser (2 moles), Leu (1 mole), Trp (1 mole), Orn (2 moles), Phe (1 mole), N-methylvaline (1 mole) and β-hydroxyaspartic acid (1 mole); and that the WAP-8294AX-13 comprised Asp (1 mole), Glu (1 mole), β-Ala (1 mole), Ser (2 moles), Leu (1 mole), Trp (1 mole), Orn (2 moles), N-methylphenylalanine (1 mole), N-methylvaline (1 mole) and β-hydroxyaspartic acid (1 mole).

EXAMPLE 12

Fatty Acid Analysis of WAP-8294AX-8, AX-9, AX-13

The WAP-8294AX-8, AX-9 and AX-13 (1 mg each) obtained in Example 10 were hydrolyzed with 6N HCl at 110° C. for 2 hours. Each hydrolyzate was extracted with ether, followed by concentration of the ether phase to dryness, dissolution of the residue in 0.1 ml of benzene: methanol (8: 2) and conversion into the methyl ester thereof at room temperature for 10 minutes by addition of a drop of trimethylsilyl diazomethane (available from Tokyo Chemical Industry Co., Ltd. ). Each methyl ester derivative was subjected to GC-MS analysis [column: DB-5 (inner diameter: 0.25 mm; length: 30 m; film thickness: 0.25 μm; available from J & W Company); temperature: 100° to 240° C. (rate of heating: 10° C./min); gas phase: helium; flow rate: 0.993 ml/min]. In any case, the retention time (9.7 minutes) in the GC analysis and m/z, as determined by EI-MS, of 187 (M$^+$ −1), 170 (M$^+$ −18), 157 (M$^+$ −31), 139 (M$^+$ −31 −18) and 103 (originated from the cleavage of $C_3$–$C_4$; a characteristic base fragment ion peak) were in agreement with those observed for the methyl ester derivative of 3-hydroxy-7-methyloctanoic acid (a fatty acid constituting the WAP-8294A$_2$). This indicates that all of the WAP-8294AX-8, AX-9 and AX-13 comprised 3-hydroxy-7-methyloctanoic acid as their fatty acid component.

EXAMPLE 13

Pharmaceutical Preparations of WAP-8294A

Typical examples of pharmaceutical preparations of the WAP-8294A will be described below.

Injection

According to the rules stipulated in General Rule for Preparations, "Injections", in The Pharmacopoeia of Japan, 12th Edition, 40 mg of the WAP-8294A hydrochloride was dissolved in 3 ml of sterilized physiological saline (Japanese Pharmacopoeia), sterilely introduced into a 3 ml volume ampule and sealed through fusion to give an injection.

Tablet

According to the rules stipulated in the General Rule for Preparations, "Tablets", there were added, to 100 mg of the WAP-8294A$_2$ hydrochloride, 65 mg of lactose (Japanese Pharmacopoeia) and 14.2 mg of starch (Japanese Pharmacopoeia) as excipients; 20 mg of Polyvinyl Pyrrolidone K25 (Japanese Pharmacopoeia) as a binder; and 0.8 mg of magnesium stearate (Japanese Pharmacopoeia) as a lubricant, followed by uniform mixing, compression molding with a tablet machine to give uncoated tablets each having a weight of 200 mg.

Ointments

According to the rules stipulated in the General Rule for Preparations, "Ointments", there were added, to 40 mg of the WAP-8294A$_2$ hydrochloride, 1.2 g of Polyethylene Glycol 4000 (Japanese Pharmacopoeia), 600 mg of Polyethylene Glycol 400 (Japanese Pharmacopoeia), 156 mg of hydrophilic vaseline (Japanese Pharmacopoeia), and 0.8 mg of propyl p-oxybenzoate (Japanese Pharmacopoeia) and 3.2 mg of ethyl p-oxybenzoate (Japanese Pharmacopoeia) as antifungal agents, followed by melting and uniform kneading with heating to give an ointment (4 g/collapsible tube).

Eye Drops

According to the rules stipulated in the General Rule for Preparations, "Eye Drops", 25 mg of the WAP-8294A$_2$ hydrochloride was dissolved in 5 ml of a 0.9% sterilized sodium chloride solution, then 0.5 mg of benzalkonium chloride (Japanese Pharmacopoeia) as a preservative was added thereto to give a uniform solution, followed by sterile filtration and sterile packaging in a 5 ml volume eye dropper to give an eye drop.

As has been described above, it is demonstrated, through the use of a small animal infection model, that the novel antibiotic WAP-8294A of the present invention has excellent therapeutic effects on infectious diseases developed by infection with Gram-positive bacteria, in particular, MRSA (methicillin-resistant Staphylococcus aureus) which has presently become a serious problem in the medical field. Therefore, the antibiotic would be effective for treating diseases including MRSA infectious diseases developed through infection with Gram-positive bacteria as infections bacteria.

What is claimed is:

1. An antibiotic WAP-8294A or pharmaceutically acceptable salt thereof having the following physicochemical properties:
   (1) Appearance: white powder;
   (2) Melting Point: 213°–220° C. (decomposed);
   (3) Solubility: soluble in water, methanol, n-butanol, dimethylformamide and dimethylsulfoxide and insoluble in acetone, ethyl acetate and chloroform;
   (4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;
   (5) Retention Time in High Performance Liquid Chromatography: 4.0 to 6.1 minutes, 8.0 minutes, 11.1 minutes, 12.5 minutes, 16.5 minutes, 17.9 minutes and 18.8 minutes;
   (6) Ultraviolet Absorption Spectrum (in water): $\lambda_{max}$: 275 nm, 280 nm, 287 nm;
   (7) Infrared Absorption Spectrum (FT-IR, KBr): Characteristic Absorption Spectrum: 3300 cm$^{-1}$, 1720~1715 cm$^{-1}$, 1636 cm$^{-1}$, 1541 cm$^{-1}$, 1404 cm$^{-1}$, 1207 cm$^{-1}$, 1137 cm$^{-1}$;
   (8) $^1$H-NMR Spectrum: (270 MHz, D$_2$O): There are observed complicated proton signals originated from methyl, methylene, methine, and heterocycles or aromatic rings;
   (9) Molecular Weight: 1,400~1,700;
   (10) Qualitative Test for Organic Compound (sodium-melting method): The antibiotic is a compound comprising carbon, hydrogen, oxygen and nitrogen elements;
   (11) Acid-complete hydrolysis provides, as ninhydrin-positive substances, Asp, Glu, Gly, Leu, Ser, Trp, Orn, N-methylvaline, β-hydroxyaspartic acid and N-methylphenylalanine;
   (12) Specific Rotation: $[\alpha]_D^{20}=+42°(c=0.5, H_2O)$;
   (13) Classification into Base, Acid and Neutral: Amphoteric.

2. An antibiotic WAP-8294A$_1$ or pharmaceutically acceptable salt thereof having the following physicochemical properties:
   (1) Appearance: white powder;
   (2) Melting Point: 215°–225° C. (decomposed);
   (3) Solubility: soluble in water, methanol, n-butanol, dimethylformamide and dimethylsulfoxide and insoluble in acetone, ethyl acetate and chloroform;
   (4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;
   (5) Retention Time in High Performance Liquid Chromatography: 8.0 minutes;
   (6) Ultraviolet Absorption Spectrum (in water): $\lambda_{max}$: 275 nm, 280 nm, 287 nm;
   (7) Infrared Absorption Spectrum (FT-IR, KBr): Characteristic Absorption Spectrum: 3300 cm$^{-1}$, 1720~1715 cm$^{-1}$, 1636 cm$^{-1}$, 1541 cm$^{-1}$, 1404 cm$^{-1}$, 1207 cm$^{-1}$, 1133 cm$^{-1}$;
   (8) Molecular Weight: 1547.9 [FAB-MS m/z 1548.9 (M+H) $^+$, m/z 1546.7 (M–H)$^-$];
   (9) Molecular Formula: $C_{72}H_{109}O_{21}N_{17}$
   (10) Acid-complete hydrolysis provides Asp (1 mole), Glu (1 mole), Gly (1 mole), Leu (1 mole), Ser (2 mole), Trp (1 mole), Orn (2 mole), N-methylvaline (1 mole), β-hydroxyaspartic acid (1 mole), N-methylphenylalanine (1 mole) and 3-hydroxyoctanoic acid (1 mole);
   (11) Specific Rotation: $[\alpha]_D^{20}=+41°$ (c=0.5, H$_2$O);
   (12) Classification into Base, Acid and Neutral: Amphoteric.

3. An antibiotic WAP-8294A$_2$ or pharmaceutically acceptable salt thereof having the following physicochemical properties:
   (1) Appearance: white powder;
   (2) Melting Point: 215°–225° C. (decomposed);
   (3) Solubility: soluble in water, methanol, n-butanol, dimethylformamide and dimethylsulfoxide and insoluble in acetone, ethyl acetate and chloroform;
   (4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;

(5) Retention Time in High Performance Liquid Chromatography: 11.1 minutes;

(6) Ultraviolet Absorption Spectrum (in water): $\lambda_{max}$: 275 nm, 280 nm, 287 nm;

(7) Infrared Absorption Spectrum (FT-IR, KBr): Characteristic Absorption Spectrum: 3300 cm$^{-1}$, 1720–1715 cm$^{-1}$, 1636 cm$^{-1}$, 1541 cm$^{-1}$, 1404 cm$^{-1}$, 1207 cm$^{-1}$, 1137 cm$^{-1}$;

(8) Molecular Weight: 1561.9 [FAB-Mass m/z 1562.9 (M+H)$^+$, m/z 1561.2 (M−H)$^-$];

(9) Molecular Formula: $C_{73}H_{111}O_{21}N_{17}$;

(10) Acid-complete hydrolysis provides, as hydrolyzates, Asp (1 mole), Glu (1 mole), Gly (1 mole), Leu (1 mole), Ser (2 mole), Trp (1 mole), Orn (2 mole), N-methylvaline (1 mole), β-hydroxyaspartic acid (1 mole), N-methylphenylalanine (1 mole) and 3-hydroxy-7-methyloctanoic acid (1 mole);

(11) Specific Rotation: $[\alpha]_D^{20}$=+42° (c=0.5, H$_2$O);

(12) Classification into Base, Acid and Neutral: Amphoteric.

4. An antibiotic WAP-8294A$_4$ or pharmaceutically acceptable salt thereof having the following physicochemical properties:

(1) Appearance: white powder;

(2) Melting Point: 215°–225° C. (decomposed);

(3) Solubility: soluble in water, methanol, n-butanol, dimethylformamide and dimethylsulfoxide and insoluble in acetone, ethyl acetate and chloroform;

(4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;

(5) Retention Time in High Performance Liquid Chromatography: 16.5 minutes;

(6) Ultraviolet Absorption Spectrum (in watera): $\lambda_{max}$: 275 rim, 280 nm, 287 nm;

(7) Infrared Absorption Spectrum (FT-IR, KBr): Characteristic Absorption Spectrum: 3300 cm$^{-1}$, 1720–1715 cm$^{-1}$, 1636 cm$^{-1}$, 1541 cm$^{-1}$, 1404 cm$^{-1}$, 1207 cm$^{-1}$, 1137 cm$^{-1}$;

(8) Molecular Weight: 1575.9 [FAB-Mass m/z 1576.9 (M+H)$^+$, m/z 1575.4 (M−H)$^-$];

(9) Molecular Formula: $C_{74}H_{113}O_{21}N_{17}$;

(10) Acid hydrolysis provides, as hydrolyzates, Asp (1 mole), Glu (1 mole), Gly (1 mole), Leu (1 mole), Ser (2 mole), Trp (1 mole), Orn (2 mole), N-methylvaline (1 mole), β-hydroxyaspartic acid (1 mole), N-methylphenylalanine (1 mole) and 3-hydroxy-8-methylnonanoic acid (1 mole);

(11) Specific Rotation: $[\alpha]_D^{20}$=+43° (c=0.5, H$_2$O);

(12) Classification into Base, Acid and Neutral: Amphoteric.

5. An antibiotic WAP-8294AX or pharmaceutically acceptable salt thereof having the following physicochemical properties:

(1) Appearance: white powder;

(2) Melting Point: 196°–200° C. (decomposed);

(3) Solubility: soluble in water, methanol, n-butanol, dimethylformamide and dimethylsulfoxide and insoluble in acetone, ethyl acetate and chloroform;

(4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;

(5) Retention Time in High Performance Liquid Chromatography: 5.3 minutes, 5.9 minutes, 6.2 minutes, 6.5 minutes, 6.9 minutes, 7.3 minutes, 8.1 minutes, 9.3 minutes, 9.8 minutes, 11.3 minutes, 12.1 minutes, 13.7 minutes and 15.0 minutes;

(6) Ultraviolet Absorption Spectrum (in water): $\lambda_{max}$: 273 nm, 280 nm, 289 nm;

(7) Infrared Absorption Spectrum (FT-IR, KBr): Characteristic Absorption Spectrum: 3300 cm$^{-1}$, 1720–1715 cm$^{-1}$, 1636 cm$^{-1}$, 1541 cm$^{-1}$, 1404 cm$^{-1}$, 1207 cm$^{-1}$, 1137 cm$^{-1}$;

(8) $^1$H-NMR Spectrum: (270 MHz, DMSO-D$_6$): There are observed complicated proton signals originated from methyl, methylene, methine, and heterocycles or aromatic rings;

(9) Molecular Weight: 1,400–1,700;

(10) Qualitative Test for Organic Compound (sodium-melting method): The antibiotic is a compound comprising carbon, hydrogen, oxygen and nitrogen elements;

(11) Acid-complete hydrolysis provides, as ninhydrin-positive substances and fatty acids, Asp, Glu, Gly, β-Ala, Leu, Ser, Trp, Orn, Val, N-methylvaline, β-hydroxyaspartic acid, Phe, N-methylphenylalanine and 3-hydroxy-7-methyloctanoic acid;

(12) Specific Rotation: $[\alpha]_D^{20}$=+24° (c=0.5, H$_2$O);

(13) Classification into Base, Acid and Neutral: Amphoteric.

6. An antibiotic WAP-8294AX-8 or pharmaceutically acceptable salt thereof having the following physicochemical properties:

(1) Appearance: white powder;

(2) Melting Point: 196°–200° C. (decomposed);

(3) Solubility: soluble in water, methanol, n-butanol, dimethylformamide and dimethylsulfoxide and insoluble in acetone, ethyl acetate and chloroform;

(4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;

(5) Retention Time in High Performance Liquid Chromatography: 9.3 minutes;

(6) Ultraviolet Absorption Spectrum (in water): $\lambda_{max}$: 273 nm, 280 nm, 289 nm;

(7) Infrared Absorption Spectrum (FT-IR, KBr): Characteristic Absorption Spectrum: 3300 cm$^{-1}$, 1720–1715 cm$^{-1}$, 1636 cm$^{-1}$, 1541 cm$^{-1}$, 1404 cm$^{-1}$, 1207 cm$^{-1}$, 1133 cm$^{31}$ $^1$;

(8) Molecular Weight: 1548 [FAB-Mass m/z 1549 (M+H)$^+$];

(9) Molecular Formula: $C_{72}H_{109}O_{21}N_{17}$;

(10) Acid-complete hydrolysis provides, as hydrolyzates, Asp (1 mole), Glu (1 mole), Gly (1 mole), Leu (1 mole), Ser (2 mole), Trp (1 mole), Orn (2 mole), Val (1 mole), β-hydroxyaspartic acid (1 mole), N-methylphenylalanine (1 mole) and 3-hydroxy-7-methyloctanoic acid (1 mole);

(11) Specific Rotation: $[\alpha]_D^{20} = +25°$ (c=0.5, H$_2$O);

(12) Classification into Base, Acid and Neutral: Amphoteric.

7. An antibiotic WAP-8294AX-9 or pharmaceutically acceptable salt thereof having the following physicochemical properties:

(1) Appearance: white powder;

(2) Melting Point: 216°–220° C. (decomposed);

(3) Solubility: soluble in water, methanol, n-butanol, dimethylformamide and dimethylsulfoxide and insoluble in acetone, ethyl acetate and chloroform;

(4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;

(5) Retention Time in High Performance Liquid Chromatography: 9.8 minutes;

(6) Ultraviolet Absorption Spectrum (in water):
$\lambda_{max}$ : 273 nm, 280 nm, 289 nm;

(7) Infrared Absorption Spectrum (FT-IR, KBr): Characteristic Absorption Spectrum: 3300 cm$^{-1}$, 1720–1715 cm$^{-1}$, 1636 cm$^{-1}$, 1541 cm$^{-1}$, 1404 cm$^{-1}$, 1207 cm$^{-1}$, 1137 cm$^{-1}$;

(8) Molecular Weight: 1548 [FAB-Mass m/z 1549 (M+H)$^+$ ; m/z 1547 (M–H)$^{-1}$ ];

(9) Molecular Formula: C$_{72}$H$_{109}$O$_{21}$N$_{17}$;

(10) Acid-complete hydrolysis provides, as hydrolyzates, Asp (1 mole), Glu (1 mole), Gly (1 mole), Leu (1 mole), Ser (2 mole), Trp (1 mole), Orn (2 mole), N-methylvaline (1 mole), β-hydroxyaspartic acid (1 mole), Phe (1 mole) and 3-hydroxy-7-methyloctanoic acid (1 mole);

(11) Specific Rotation: $[\alpha]_D^{20} = +28°$ (c=0.5, H$_2$O);

(12) Classification into Base, Acid and Neutral: Amphoteric.

8. An antibiotic WAP-8294AX-13 or pharmaceutically acceptable salt thereof having the following physicochemical properties:

(1) Appearance: white powder;

(2) Melting Point: 205°–210° C. (decomposed);

(3) Solubility: soluble in water, methanol, n-butanol, dimethylformamide and dimethylsulfoxide and insoluble in acetone, ethyl acetate and chloroform;

(4) Color Reaction: positive in ninhydrin, Ehrlich, Rydon-Smith, potassium permanganate aqueous solution, sulfuric acid and iodine vapor reactions and exhibiting quenching spots through irradiation with light rays of 254 nm emitted from a UV lamp; negative in Molisch, silver nitrate, ferric chloride and Dragendorff's reactions;

(5) Retention Time in High Performance Liquid Chromatography: 15.0 minutes;

(6) Ultraviolet Absorption Spectrum (in water):
$\lambda_{max}$ : 273 nm, 280 nm, 289 nm;

(7) Infrared Absorption Spectrum (FT-IR, KBr): Characteristic Absorption Spectrum: 3300 cm$^{-1}$, 1720–1715 cm$^{-1}$, 1636 cm$^{-1}$, 1541 cm$^{-1}$, 1404 cm$^{-1}$, 1207 cm$^{-1}$, 1137 cm$^{-1}$;

(8) Molecular Weight: 1576 [FAB-Mass m/z 1577 (M+H)$^+$ ];

(9) Molecular Formula: C$_{74}$H$_{113}$O$_{21}$N$_{17}$;

(10) Acid-complete hydrolysis provides, as hydrolyzates, Asp (1 mole), Glu (1 mole), B -Ala (1 mole), Leu (1 mole), Ser (2 mole), Trp (1 mole), Orn (2 mole), N-methylvaline (1 mole), β-hydroxyaspartic acid (1 mole), N-methylphenylalanine (1 mole) and 3-hydroxy-7-methyloctanoic acid (1 mole);

(11) Specific Rotation: $[\alpha]_D^{20} = +27°$ (c=0.5, H$_2$O);

(12) Classification into Base, Acid and Neutral: Amphoteric.

9. A method for producing an antibiotic WAP-8294A as set forth in any one of claims 1 to 8 comprising the steps of cultivating, in a culture medium, a microorganism belonging to the genus *Lysobacter* and having an ability of producing the antibiotic WAP-8294A as set forth in any one of claims 1 to 8 to produce the antibiotic and accumulate it in the culture medium; then recovering the antibiotic.

10. An isolated microorganism belonging to the genus *Lysobacter* which produces the antibiotic WAP-8294A.

11. The isolated microorganism of claim 10 which is *Lysobacter* sp. WAP-8294.

12. An antibacterial composition comprising a pharmaceutically acceptable carrier and at least one antibiotic selected from the group consisting of WAP-8294A, WAP-8294A$_1$, WAP-8294A$_2$, WAP-8294A$_4$, WAP-8294AX, WAP-8294AX-8, WAP-8294AX-9 and WAP-8294AX-13 and pharmaceutically acceptable salts thereof.

* * * * *